(12) United States Patent
Kurita et al.

(10) Patent No.: US 7,847,145 B2
(45) Date of Patent: Dec. 7, 2010

(54) BODY FLUID ABSORBENT ARTICLE

(75) Inventors: Yuka Kurita, Sakura (JP); Kazunori Nishizawa, Sakura (JP)

(73) Assignee: Daio Paper Corporation, Ehime (JP)

( * ) Notice: Subject to any disclaimer, the term of this patent is extended or adjusted under 35 U.S.C. 154(b) by 1151 days.

(21) Appl. No.: 10/551,532

(22) PCT Filed: Mar. 29, 2004

(86) PCT No.: PCT/JP2004/004443

§ 371 (c)(1),
(2), (4) Date: Dec. 23, 2005

(87) PCT Pub. No.: WO2004/087028

PCT Pub. Date: Oct. 14, 2004

(65) Prior Publication Data

US 2006/0116651 A1 Jun. 1, 2006

(30) Foreign Application Priority Data

| Mar. 31, 2003 | (JP) | ............................... 2003-94627 |
| Mar. 31, 2003 | (JP) | ............................... 2003-94628 |
| Mar. 31, 2003 | (JP) | ............................... 2003-094629 |

(51) Int. Cl.
*A61F 13/15* (2006.01)
*A61F 13/20* (2006.01)

(52) U.S. Cl. ..................... 604/378; 604/364; 604/381; 604/382; 604/385.101

(58) Field of Classification Search .................. 604/364, 604/378, 381

See application file for complete search history.

(56) References Cited

U.S. PATENT DOCUMENTS

| 2,546,705 | A | * | 3/1951 | Strawinski | ............... 428/297.7 |
| 2,681,032 | A | * | 6/1954 | Shaw | ......................... 116/200 |
| 2,964,040 | A | * | 12/1960 | Morse et al. | ................. 604/366 |
| 3,546,716 | A | * | 12/1970 | Laumann | ....................... 4/452 |
| 3,651,809 | A | * | 3/1972 | Champaigne, Jr. | .......... 604/364 |
| 4,357,938 | A | * | 11/1982 | Ito et al. | ..................... 604/376 |
| 4,418,524 | A | * | 12/1983 | Ito et al. | ........................ 57/239 |
| 4,447,240 | A | * | 5/1984 | Ito et al. | ................. 604/385.23 |
| 4,623,342 | A | * | 11/1986 | Ito et al. | ................. 604/385.23 |
| 4,809,493 | A | * | 3/1989 | Genba et al. | .................. 57/238 |
| 4,834,733 | A | * | 5/1989 | Huntoon et al. | ............. 604/361 |
| 5,151,091 | A | * | 9/1992 | Glaug et al. | ........... 604/385.101 |
| 5,300,358 | A | * | 4/1994 | Evers | ......................... 442/396 |

(Continued)

FOREIGN PATENT DOCUMENTS

EP 0815821 1/1998

(Continued)

*Primary Examiner*—Tatyana Zalukaeva
*Assistant Examiner*—Susan Su
(74) *Attorney, Agent, or Firm*—William L. Androlia; H. Henry Koda

(57) ABSTRACT

The present invention relates to a technique for a body fluid absorbent article including a moving absorbent, capable of using a wider range of the absorbent for absorption and efficiently moving the absorbent. The present invention is characterized in that the absorbent 25 including a body fluid absorption and holding function and a shrinkage function when contacting with a body fluid is provided in a body fluid absorbent portion, and an absorption control layer 40 a liquid impermeable range of which is reduced whenever the body fluid is excreted is provided on the absorbent 25.

12 Claims, 37 Drawing Sheets

U.S. PATENT DOCUMENTS

| | | | |
|---|---|---|---|
| 5,399,175 A * | 3/1995 | Glaug et al. | 604/385.101 |
| 5,472,518 A * | 12/1995 | Patnode et al. | 134/34 |
| 5,496,626 A * | 3/1996 | Hamajima et al. | 442/412 |
| 5,785,695 A * | 7/1998 | Sato et al. | 604/339 |
| 5,821,179 A * | 10/1998 | Masaki et al. | 442/375 |
| 5,885,264 A * | 3/1999 | Matsushita | 604/361 |
| 6,293,935 B1 * | 9/2001 | Kimura et al. | 604/387 |
| 6,423,883 B1 * | 7/2002 | Morman et al. | 604/368 |
| 6,432,097 B1 * | 8/2002 | Ahr et al. | 604/385.19 |
| 6,461,338 B1 * | 10/2002 | Shimoe et al. | 604/385.01 |
| 6,551,297 B2 * | 4/2003 | Tanaka et al. | 604/385.24 |
| 6,695,827 B2 * | 2/2004 | Chen et al. | 604/385.01 |
| 6,955,667 B1 * | 10/2005 | Tanaka et al. | 604/385.24 |
| 2001/0008964 A1 * | 7/2001 | Kurata et al. | 604/364 |
| 2002/0128625 A1 * | 9/2002 | Tanaka et al. | 604/385.28 |
| 2004/0039363 A1 * | 2/2004 | Sugiyama et al. | 604/385.101 |
| 2004/0147896 A1 * | 7/2004 | Mizutani et al. | 604/385.17 |
| 2007/0239132 A1 * | 10/2007 | Mishima | 604/385.101 |

FOREIGN PATENT DOCUMENTS

| | | |
|---|---|---|
| EP | 0846454 | 6/1998 |
| GB | 2838957 | 7/2003 |
| JP | H7-189197 | 7/1995 |
| JP | H8-511706 | 12/1996 |
| JP | 2000-510031 | 8/2000 |
| JP | 2005-510033 | 8/2000 |
| JP | 2001-137286 | 5/2001 |
| JP | 2002-224162 | 8/2002 |
| JP | 2003-038568 | 2/2003 |
| JP | 2003-52748 | 2/2003 |
| WO | WO 95/00093 | 1/1995 |
| WO | WO 00/00145 | 1/2000 |
| WO | WO 02/062279 | 8/2002 |

* cited by examiner (a)

(b)

(a)

(b)

(a)

(b)

(a)

(b)

BODY FLUID ABSORBENT ARTICLE

TECHNICAL FIELD

The present invention relates to a body fluid absorbent article such as a disposable diaper or a sanitary napkin.

BACKGROUND ART

A body fluid absorbent article normally includes a liquid permeable surface layer provided on a side in contact with a body skin, a leak-proof layer provided on a side farther from the body skin, and a body fluid absorbent portion provided between the surface layer and the leak-proof layer.

In this case, various compositions are known as a composition of the body fluid absorbent portion. The body fluid absorbent portion mainly consists of an absorbent material such as a super absorbent polymer, flocculent pulp (flap pulp), or crape paper. Following recent advancement of a super absorbent polymer technique, it is possible to form a thinner body fluid absorbent portion. Body fitting performance of the absorbent portion of the product is, therefore, improved and leakage of a body fluid is reduced accordingly.

The improved absorbing performance, in turn, causes consumers to demand developing a new product that is thin but high in absorbing capacity and that can be used for a long time.

To meet this demand, the body fluid absorbent portion is required to absorb a large amount of urine, for example, excreted many times. Nevertheless, whenever urination repeatedly occurs, an absorption speed of the body fluid absorbent portion is decreased, with the result the body fluid cannot be often absorbed by the body fluid absorbent portion, particularly longitudinal ends thereof. Reasons for this are considered as follows. Diffusion of the body fluid in a longitudinal direction (of the product) is slow or insufficient and a phenomenon so-called "gel blocking" occurs that the super absorbent polymer so swells as to inhibit liquid diffusion and wetting of the super absorbent polymer.

To solve these phenomena, a technique for assisting in wetting and diffusion in the longitudinal direction, a technique for preventing the gel blocking of the super absorbent polymer, an attempt to improve a form and incorporation of the super absorbent polymer, a method for securing a space in which an absorbent material swells by wetting, and the like have been proposed as disclosed in, for example, Patent Koho (Japanese Unexamined Patent Publication of Translated Version) Nos. 2000-510031 and 2000-510033.

However, none of these methods find satisfactory solutions to these disadvantages. When these causes are considered again, it is found that the body fluid absorbent portion of the conventional body fluid absorbent article is elongated and arranged in the longitudinal direction of the product on the premise that the body fluid from a discharge region wets and spreads (diffuses) up to the longitudinal ends of the portion. Therefore, as long as the diffusion of the body fluid in the longitudinal direction is insufficient, the entire body fluid absorbent portion is substantially incapable of absorbing the body fluid.

On the other hand, taking into account that there is a limit to the diffusion of the body fluid within the body fluid absorbent portion, the inventors of the present invention have proposed various body fluid absorbent articles each configured so that an absorbent material portion corresponding to a body fluid receiving portion is updated by allowing shrinkage and movement of the absorbent material when the absorbent material contacts with the body fluid, and improved techniques therefor so as to solve these disadvantages. Specifically, examples of these include a proposal disclosed in International Publication PCT/JP02/00833 filed by the applicant of the present invention.

According to this conventional technique, it is possible to provide a body fluid absorbent article that can make effective use of an entire absorbent or, more generally, a body fluid absorbent article that is high in absorbing capacity, that can sufficiently absorb the body fluid a plurality of times, and that can eventually ensure a long-time use.

This conventional technique, however, still leaves rooms for improvements in use of the absorbent material in a wider range for absorption and efficient movement of the absorbent.

DISCLOSURE OF THE INVENTION

It is, therefore, a main object of the present invention to provide a technique capable of using an absorbent in a wider range for absorption and a technique capable of efficiently moving the absorbent.

These objects are attained by providing an absorbent that includes a body fluid absorption and holding function and a shrinkage function when contact with a body fluid in a body fluid absorbent portion, and providing an absorption control layer a liquid impermeable range of which is reduced whenever a body fluid is excreted on the absorbent.

According to the present invention, when the body fluid excreted from the body is absorbed by the absorbent, the shrinkage function is performed in a body fluid contact portion of the absorbent. As a result, the absorbent is moved. Namely, the portion of the absorbent which portion contacts first with the body fluid is moved and replaced by a new region of the absorbent, that is, the absorbent is updated whenever the body fluid is excreted. Even in this case, the entire absorbent is not always used effectively.

As a technique for diffusing the body fluid, there is conventionally proposed a technique for providing a fiber assembly layer or a diffusion space having a body fluid diffusion function on the absorbent. However, even if only this technique is applied, body fluid absorption by the absorbent still proceeds so as to spread around the portion of the absorbent with which portion the excreted body fluid contacts first. Naturally, therefore, there is a limit to making effective use of the absorbent.

According to the present invention, by contrast, if the absorption control layer the liquid impermeable range of which is reduced whenever the body fluid is excreted is provided, then the body fluid directed to the absorbent is diffused around the liquid impermeable range and absorbed by the absorbent out of the liquid impermeable range. Compared with the conventional technique, therefore, the absorbent in a wider range is used.

Since this liquid impermeable range is reduced whenever the body fluid is excreted, a next range in which the body fluid is introduced to the absorbent is a range inside the previous body fluid supply region and outside the reduced liquid impermeable range. Namely, the region of the absorbent to which the body fluid is introduced is changed whenever the body fluid is excreted and the diffusion range of the body fluid is reduced, accordingly. As a result, whenever the excretion occur, the body fluid can be supplied to a region of the absorbent that does not absorb the body fluid yet or that has sufficiently surplus absorbing force. It is, therefore, possible to ensure making effective use of the absorbent. Further, for this reason, even after the body fluid is excreted a plurality of times, it is difficult to deteriorate absorbing performance due to the gel blocking or the like. This can further ensure making effective use of the absorbent. In addition, a constant tendency that the diffusion range of the body fluid is reduced whenever the body fluid is excreted can contribute to facilitating setting of a body fluid diffused state.

According to the present invention, therefore, the size and the arrangement of the liquid impermeable range as well as the number of liquid impermeable ranges and the like can be appropriately set according to the intended body fluid diffused state (e.g., how much degree the body fluid is diffused in a longitudinal direction and a width direction of the article) and according to the degree of reduction of the liquid impermeable range whenever the excretion occurs. It is thereby possible to ensure controlling the diffusion of the body fluid and make sufficiently use of the absorbent. Although the liquid impermeable range of the present invention can be appropriately set as stated, it is particularly preferable that the liquid impermeable range includes a body fluid receiving portion defined as a range in which the excreted body fluid is first received within the body fluid absorbent portion.

According to the present invention, the excreted body fluid is not absorbed but diffused by the liquid impermeable range. If no channel for this diffusion is provided, the wearer feels uncomfortable. It is, therefore, preferable to provide a body fluid diffusion layer which covers the liquid impermeable range and at least a part of which protrudes outside the liquid impermeable range. If so, the excreted body fluid is introduced to the outside of the liquid impermeable range through the body fluid diffusion layer and absorbed by the absorbent.

According to the present invention, it is possible to adopt a structure in which the entire absorbent is not fixed to any part. In this case, however, it is difficult to move the absorbent as intended. According to the present invention, therefore, it is preferable that the absorbent includes a fixed portion fixed to the article, and a free portion that is not fixed to the article. If so, it is preferable to provide an absorption control layer that is reduced from a fixed portion side of the absorbent toward a free portion side thereof whenever the body fluid is excreted.

In this embodiment, the body fluid directed to the absorbent is blocked by the liquid impermeable range of the absorption control layer and diffused around the liquid impermeable range without being absorbed by the absorbent. Among the body fluid, the body fluid diffused to the fixed portion-side is supplied to a fixed portion-side region of the absorbent in which region the body fluid is not originally blocked by the liquid impermeable range or in which range the body fluid is not blocked by the liquid impermeable range due to the reduction thereof. As a result, the body fluid is preferentially supplied to the fixed portion-side region of the absorbent rather than a region of the absorbent corresponding to the body fluid receiving portion and preferentially absorbed by the fixed portion-side region of the absorbent, and the fixed portion-side region preferentially shrinks. According to the present invention, the liquid impermeable range is reduced from the fixed portion-side to the free portion-side of the absorbent whenever the body fluid is excreted. Therefore, when the next excretion occurs, the body fluid in the region of the absorbent which does not absorb the body fluid yet or which has sufficiently surplus absorbing force even after absorbing the body fluid is not blocked by the liquid impermeable range, and the body fluid absorption function and the shrinkage function are fulfilled in the region.

If one end of the absorbent is fixed, it is preferable that the absorbent is elongated and includes the fixed portion on the one end, and that the absorption control layer is a cylindrical member including the liquid impermeable range continuous in a circumferential direction and a longitudinal direction, the absorbent being inserted into an inner cavity of the absorption control layer. By thus inserting the absorbent into the inner cavity of the cylindrical absorption control layer having the liquid impermeable range continuous in the circumferential direction and the longitudinal direction, it is possible to ensure blocking the contact between the absorbent and the body fluid.

If one end of the absorbent is fixed, it is preferable that the absorption control layer is configured so as not to block at least a contact between a fixed portion-side end of the free portion of the absorbent and the body fluid. If the supply of the body fluid to the fixed portion-side end of the free portion of the absorbent is blocked by the liquid impermeable range of the absorption control layer, the body fluid is supplied to the absorbent after the liquid impermeable range is reduced. This may possibly hamper prompt and smooth initial absorption, shrinkage, and movement.

If one end of the absorbent is fixed and a body fluid diffusion layer is provided, it is preferable to provide the body fluid diffusion layer so as to extend at least from the body fluid receiving portion defined as the range in which the excreted body fluid is received first within the body fluid absorbent portion to the fixed portion-side end of the free portion of the absorbent. By doing so, it is possible to smoothly and surely supply the body fluid to the fixed portion-side end of the free portion of the absorbent.

The absorbent of the present invention is blocked from contacting with the body fluid by the liquid impermeable range of the absorption control layer. Due to this, in a preferred aspect, the body fluid diffusion layer is provided. However, a body fluid supply speed is faster than a body fluid diffusion speed. If the body fluid received in the body fluid receiving portion is not temporarily stored, it may possibly go backward to the body skin. It is, therefore, preferable that if the body fluid diffusion layer is provided, a body fluid storage portion that contacts with the body fluid diffusion layer is provided in the body fluid receiving portion defined as the range in which the excreted body fluid is received first within the body fluid receiving portion.

The body fluid diffusion layer of the present invention preferably has diffusibility capable of promptly raising the body fluid along an inclined curved surface of the article. From this point of view, it I preferable that the body fluid diffusion layer of the present invention consists of a fiber assembly sheet having a Klemm water absorption according to "Testing Method for Water Absorption of Paper and Paperboard by Klemm Method" specified in JIS P 8141, which absorption is 100 millimeters or more in ten minutes.

An ordinary body fluid absorbent article includes a liquid permeable surface layer provided on a side facing the body skin, and a leak-proof layer provided on a side apart from the body skin, and the body fluid absorbent portion is provided between the surface layer and the leak-proof layer. In this case, the liquid impermeable range preferably includes at least the body fluid receiving portion defined as the range in which the excreted body fluid is received first within the body fluid absorbent portion.

The absorption control layer of the present invention can be proposed in various forms. A first form of the absorption control layer is a liquid impermeable, water soluble layer peripheral portions of which are dissolved whenever the body fluid is excreted. The liquid impermeable range is formed entirely by this absorption control layer. This is preferable because only by covering the absorbent in the body fluid receiving portion, the liquid impermeable range can easily demonstrate a function of being reduced whenever the body fluid excreted at low cost.

As a specific example of this first absorption control layer, there is proposed a water soluble film having an absorbent-side surface that is not subjected to a water repellent treatment and an opposite surface to the absorbent-side surface and subjected to the water repellent treatment. Such a water soluble film forms the liquid impermeable range as a whole by the water repellent treatment, and the surface opposite to the absorbent-side surface and subjected to water repellent treatment is not dissolved even if contacting with the body fluid. Thus, the body fluid is not permeated by the water-repellent treated surface of the film but diffuse even if the body fluid reaches the surface. The body fluid is carried toward the absorbent-side surface from the surroundings of the film, and the film is dissolved when the body fluid contacts with the untreated surface. Accordingly, the entire film that constitutes the liquid impermeable range is dissolved and reduced whenever the body fluid is excreted.

As a second absorption control layer, there is proposed a liquid impermeable sheet which shrinks by 50% or more in area when being wet. This liquid impermeable sheet forms the liquid impermeable range as a whole, and the sheet is not dissolved but shrinks when being wet. The liquid impermeable range is, therefore, reduced whenever the body fluid is excreted.

As a third absorption control layer, there is proposed a liquid impermeable sheet integrated with a shrinkable member that shrinks when in contact with the body fluid. Even if a sheet that does not shrink even when in contact with the body fluid such as a polyethylene sheet, a nonwoven fabric subjected to the water repellent treatment or the like as frequently used in the field of body fluid absorbent articles is employed, the sheet can function as the absorption control layer the liquid impermeable range of which is reduced whenever the body fluid is excreted by integrating the sheet with a shrinkable member that shrinks when in contact with the body fluid.

As a fourth absorption control layer, there is proposed a liquid permeable sheet which is subjected to a water repellent treatment, and water repellency of which is lost when contacting with the body fluid for a predetermined time or more.

A body fluid permeable sheet such as a hydrophilic nonwoven fabric is subjected to the water repellent treatment so that the water repellency is lost when the sheet contacts with the body fluid for predetermined time or more, whereby even the sheet exhibits the body fluid permeability in the region which lost the water repellency. Due to this, although the sheet is not reduced per se, the liquid impermeable range is reduced. It is, therefore, possible to suitably use this sheet as the absorption control layer the liquid impermeable range of which is reduced whenever the body fluid is exereted.

Meanwhile, to allow the absorbent and the absorption control layer to effectively function, it is important that a moving resistance of the absorbent is low and the body fluid is smoothly distributed along the absorbent and the absorption control layer. According to the present invention, therefore, it is preferable that a plurality of wall members are arranged within the body fluid absorbent portion at predetermined intervals, and that the absorbent and the absorption control layer are arranged between the wall members.

If the absorbent and the absorption control layer are arranged between the wall members, these wall members can resist the pressure from the side facing the body skin. During the time the wall members resist the pressure, an absorbent shrinking space and a body fluid distribution channel are secured. Due to this, even if external pressure applied to the absorbent side from the wearer side is high, the absorbent shrinking space and the body fluid distribution channels are surely secured when the wearer wears the article. The absorbent can, therefore, surely and efficiently shrink and the body fluid can be efficiently absorbed.

According to the present invention, particularly since the liquid impermeable range is present in the absorption control layer, the body fluid that reaches the interior of the body fluid absorbent portion is not promptly absorbed by the absorbent. It is considerably advantageous to secure such a body fluid distribution channel. If the liquid impermeable range is reduced by the shrinking of the absorption control layer, a space for the shrinking is also secured by the wall members. Further, the wall members suppress the diffusion of the body fluid in a traversing direction whether the wall members are liquid permeable or liquid impermeable, thereby accelerating the diffusion along the wall members. Accordingly, it is also advantageous to secure the body fluid distribution channel in that the certainty and efficiency of the distribution of the body fluid to the fixed portion of the absorbent are improved irrespective of the position of the fixed portion.

As can be understood from the advantages of the wall members, it is quite important to provide the wall members if the absorbent in a wider range is to be used for absorption and to be efficiently moved. Due to this, the applicant of the present invention proposed a wall member consisting of a liquid impermeable bag body into which super absorbent polymers are filled in the International Publication PCT/JP02/00833. The super absorbent polymers in this wall member expand and the wall member resists the external pressure when the article is used to thereby secure the absorbent shrinking space and the body fluid distribution space. The wall member is, therefore, desired to have a sufficiently high strength.

According to the present invention, therefore, there is provided body fluid absorbent article comprising: a wall member consisting of a liquid permeable bag body into which super absorbent polymers are filled; and an absorbent including a body fluid absorption and holding function and a shrinkage function when contacting with a body fluid, wherein the bag body has a bursting strength equal to or higher than 200 g/cm$^2$ according to Mullen Burst Test specified in JIS L 1096A in a standard state.

According to the present invention, the body fluid that reaches the interior of the body fluid absorbent portion is absorbed by the wall members and a thickness of each wall member is increased by expansion of the super absorbent polymers within the wall member. At this time, if a material having a bursting strength equal to or higher than 200 g/cm$^2$ according to Mullen Burst Test specified in JIS L 1096A in a standard state is used as the bag body of the wall member, even an article such as an adult paper diaper the external pressure of which may possibly be extremely high can sufficiently resist a burst.

In the present invention, "the bag body has a bursting strength equal to or higher than 200 g/cm$^2$ according to Mullen Burst Test . . . " means that a test sheet equivalent to a sheet that consists of the bag body is formed and a value measured by the Mullen Burst Test for this test sheet falls within the above-stated range. Accordingly, as the bag body including bonded portions as will be described in the embodiments, a test sheet that does not include bonded portions is formed using the same material as that for the bag body and a test sheet that includes bonded portions equal in configuration to the bag body are manufactured, and values measured by the Mullen Test Method for the both test sheets fall within the above-stated range, respectively. Such sheets correspond to the bag body of the present invention.

Such wall members are suitable for the body fluid absorbent article including the moved absorbent. If the wall members and the absorbent moved when in contact with the body fluid are provided in the body fluid absorbent portion, the absorbent shrinking and moving space is secured by the wall members. It is, therefore, possible to further ensure exhibiting the absorbent shrinking and moving function. The advantages obtained when the present invention is applied to the configuration in which a plurality of wall members are provided at predetermined intervals and in which the absorbent is provided between the wall members are already described above. If the material having a bursting strength equal to or higher than 200 g/cm² according to Mullen Burst Test specified in JIS L 1096A in a standard state is used as the bag body of the wall member, these advantages can be exhibited more surely.

If a large amount of super absorbent polymers are filled into the bag body of the wall member, the internal pressure of the bag body is increased and the space securing function against the external pressure is increased when the super absorbent polymers absorbs the body fluid and expand. However, there is a high probability that the bag body bursts when the external pressure is applied if strength of the bag body is low. By contrast, if the bag body having the bursting strength within the range of the present invention is used, a large amount of body fluid is absorbed. Therefore, it is possible to sufficiently resist the burst even if the bag body as the wall member is used which is filled with 300 grams or more of super absorbent polymers per unit area (1 m² of the bag body in a flattened state).

According to a preferred embodiment, the wall members and the absorbent are arranged in the longitudinal direction of the article, and one side end of the absorbent in the longitudinal direction of the article is fixed to the article. In this case, thanks to the presence of the wall members, lateral leakage can be prevented, the diffusion of the body fluid in the longitudinal direction of the article can be accelerated, and moving efficiency can be improved by acceleration of the diffusion of the body fluid to the fixed portion-side. On the other hand, however, the absorbent is quite long and required to be curvilinearly moved in the hip joint part, and the moving resistance is quite high. In this case, to reduce the moving resistance, the shrinking space needs to be secured further surely and the bag body is desired to be sufficiently high in strength. Even in such an embodiment, it is preferable to use the bag body having the bursting strength in the range of the present invention.

BEST MODE FOR CARRYING OUT THE INVENTION

Figure 1:
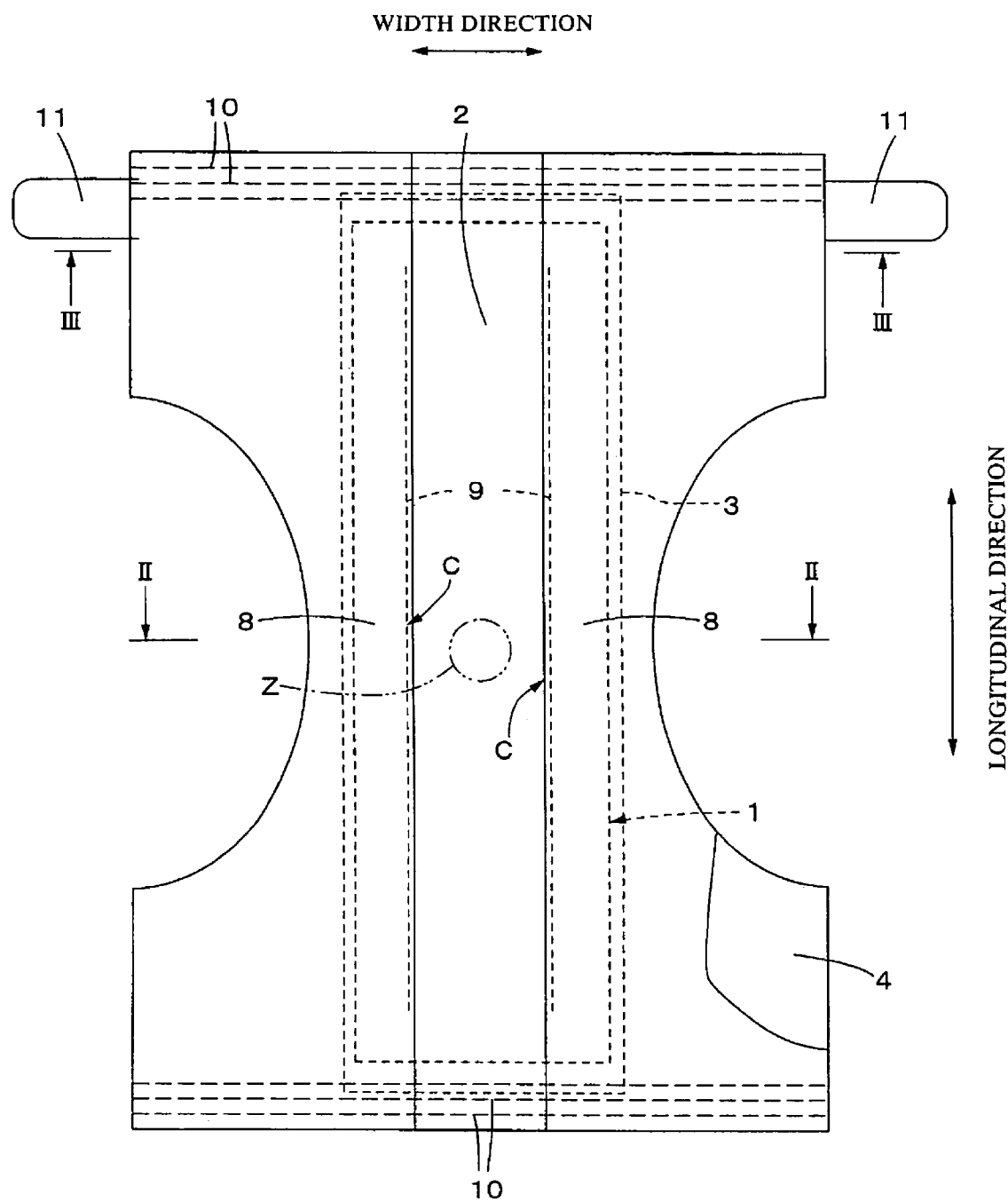
FIG. 1 is a plan view that depicts a surface layer side of an exemplary disposable paper diaper in an unfolded state according to the present invention.

An embodiment of the present invention will be described hereinafter in detail based on examples of applying the present invention to a so-called tape type paper diaper configured so that right and left back sides of the diaper are brought into right and left abdomen sides thereof and bonded thereto by a tape fastener (including an adhesive tape fastener and a surface fastener) when a user uses (wears) the diaper. The present invention is generally applied to body fluid absorbent articles such as a disposable diaper and a sanitary napkin. If the examples of applying the present invention to the tape type paper diaper are described, it is considered that embodiments in relation to a briefs type paper diaper, a pad type disposable absorbent article, and the sanitary napkin can be easily estimated. The latter two examples will not be, therefore, described herein.

FIGS. 1 to 5 depict examples of the disposable diaper to which the present invention is applied. This disposable diaper includes a rectangular surface layer 2 that is provided on a side in contact with the body skin, that consists of a liquid permeable nonwoven fabric sheet, a porous film sheet or the like, and that directly contacts with the wearer's skin, a rectangular leak-proof layer 3 that is provided on a side farther from the body skin and that consists of a liquid impermeable back sheet or the like, and a body fluid absorbent portion 1 that is provided between the layers 2 and 3 and that includes a body fluid receiving portion Z defined as a range in which an excreted body fluid is first permeated by the surface layer.

The disposable diaper also includes a flexible external sheet 4 on a back side of a product that is a back side relative to the leak-proof layer 3. This external sheet 4 consists of one nonwoven fabric or a plurality of fixedly superimposed air-permeable and water-repellent nonwoven fabrics.

Leg standing cuffs C protruding to a used surface side are formed on both sides of the product, respectively. Each of these standing cuffs C is configured by a standing sheet 8 that is substantially continuous in a width direction and one or a plurality of expansion members 9 consisting of, for example, thread rubber. More specifically, the standing cuff C is formed by doubling the standing sheet 8 while wrapping up the expansion member 9 in the sheets 8 and fixedly bonding the expansion member 9 to the sheet 8. The standing sheet 8 that constitutes each standing cuff C is preferably not liquid permeable but liquid impermeable or hydrophobic. In addition, the standing sheet may be formed by subjecting a liquid permeable sheet such as a nonwoven fabric to a silicon treatment or the like so that the sheet exhibits a liquid repellent property. It is also preferable that the standing sheet 8 is air permeable or steam permeable. If a liquid impermeable film sheet is put between the doubled standing sheets 8, a leak proof performance can be further improved.

Interiors of the doubled standing sheets 8 are fixedly bonded to the surface layer 2 and the external sheet 4 by a hot melt adhesive or the like. As a result, a bonding starting end of the doubled standing sheets 8 forms a standing end of the standing cuff C. Tip end sides from this standing end are free parts that are not fixed to a product main body.

Longitudinal ends of the doubled standing sheets 8 are fixed to the article or, more specifically, to an outer surface of the surface layer 2 in a state in which tip ends of the free parts are directed toward a center of the article. A space surrounded by the right and left standing cuffs C forms a urine or loose passage confinement space. If the urine is excreted into this space, then the urine is absorbed into the body fluid absorbent portion 1 past the liquid permeable surface layer 2 or solid components of the loose passage are prevented from over-passing the article by the standing cuffs C serving as barriers.

On longitudinal ends of a front body and a back body, waist expansion members 10 consisting of thin thread rubber are arranged in parallel between the nonwoven fabrics of the external sheet 4 on edges of waist openings at intervals so as to improve a fitting performance around the waist. The interval and number of the waist expansion members 10 can be appropriately set. The interval is preferably, for example, about four to eight millimeters and the number is preferably, for example, about three to ten. Reference symbol 11 denotes a tape fastener for bringing the right and left back sides into the right and left abdomen sides and bonding them.

In the paper diaper according to this embodiment, absorbents 25 (specific examples of which will be described later) each of which includes a body fluid absorption and holding function and a shrinkage function when contacting the body fluid are provided in the body fluid absorbent portion 1. Each of these absorbents 25 includes a fixed portion 30 fixed to the article and a free portion 31 unfixed to the article. The absorbents 25 also includes an absorption control layer 40 having a liquid impermeable range that interrupts contact between the absorbent 25 and the body fluid at least in the body fluid receiving portion Z and that is reduced from the fixed portion 30 side of the absorbent 25 toward a moving side whenever the body fluid is excreted. The body fluid absorbent portion 1 can be arbitrarily set. Normally, the body fluid absorbent portion 1 is a rectangular range including the body fluid receiving portion, and has a length about 50 to 100% of that of the article in the longitudinal direction of the article and a width equal to or higher than 70% of that of a hip joint part of the article.

Figure 2:
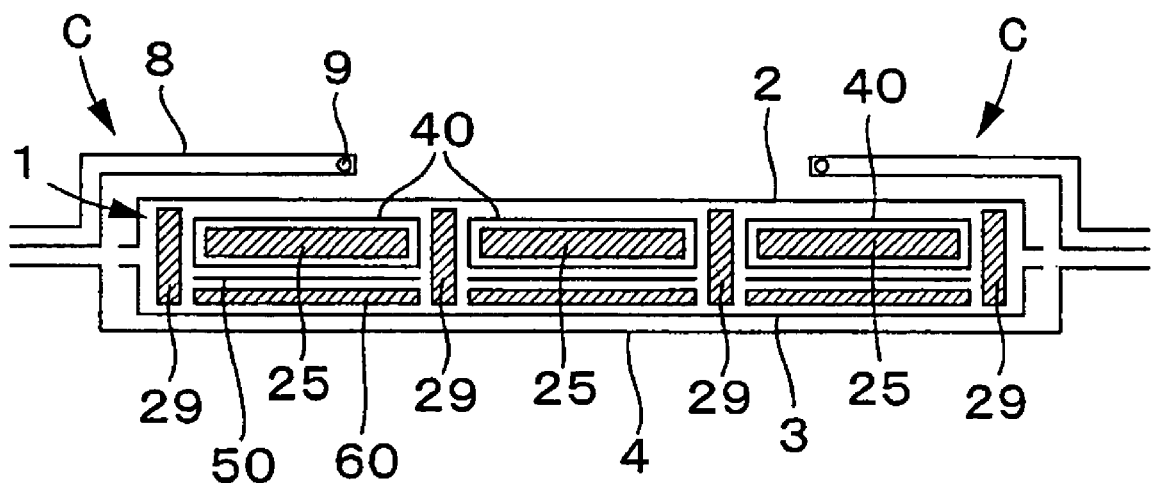
FIG. 2 is a schematic cross-sectional view taken along a line II-II of FIG. 1.
Figure 3:
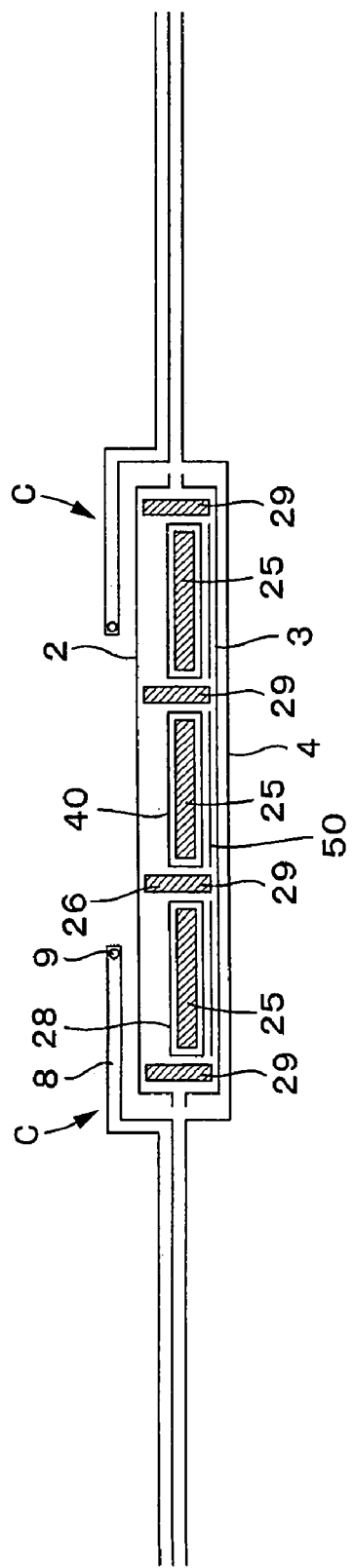
FIG. 3 is a schematic cross-sectional view taken along a line III-III of FIG. 1.
Figure 4:
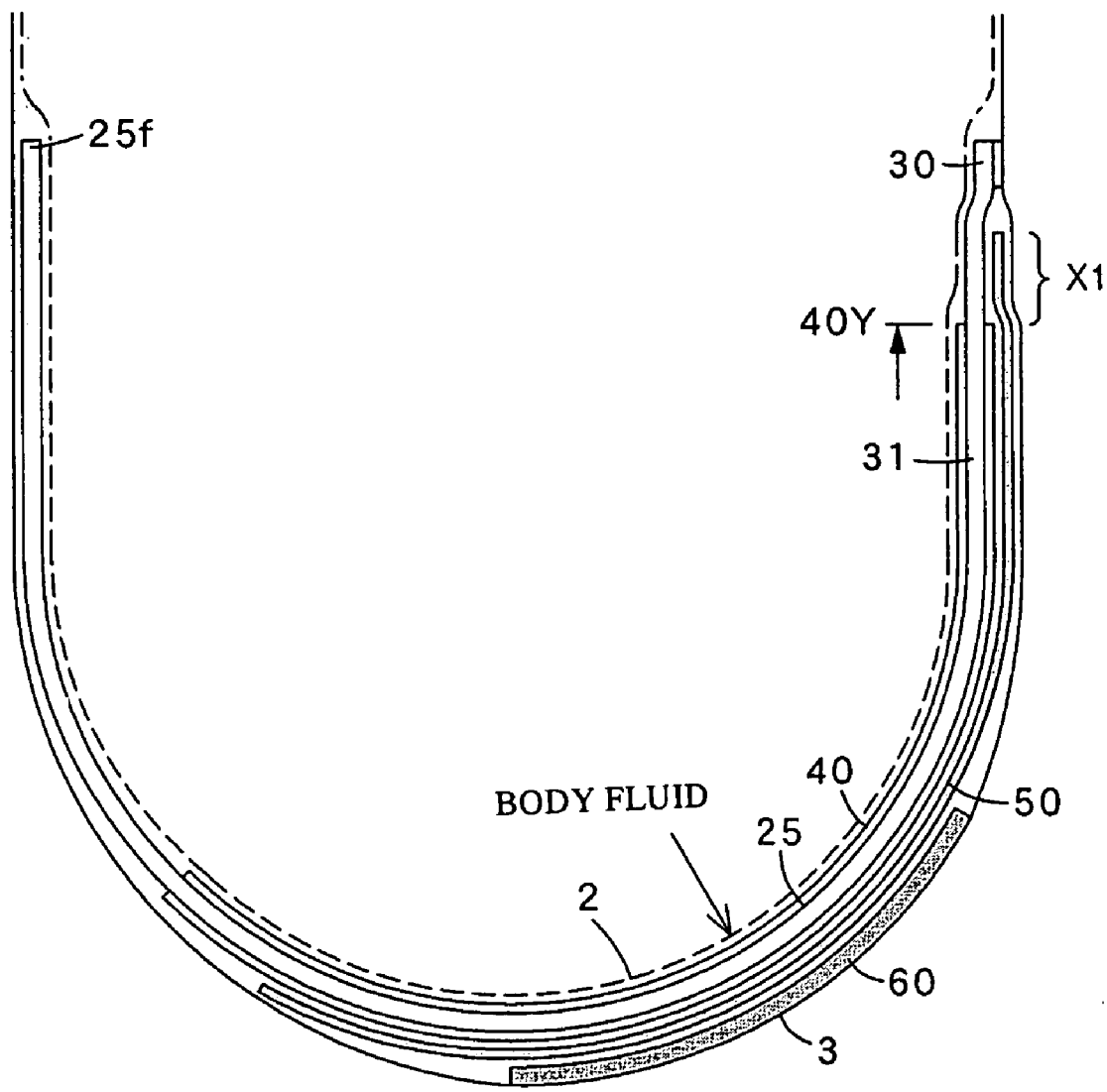
FIG. 4 is a schematic longitudinal sectional view of a paper diaper.
Figure 5:
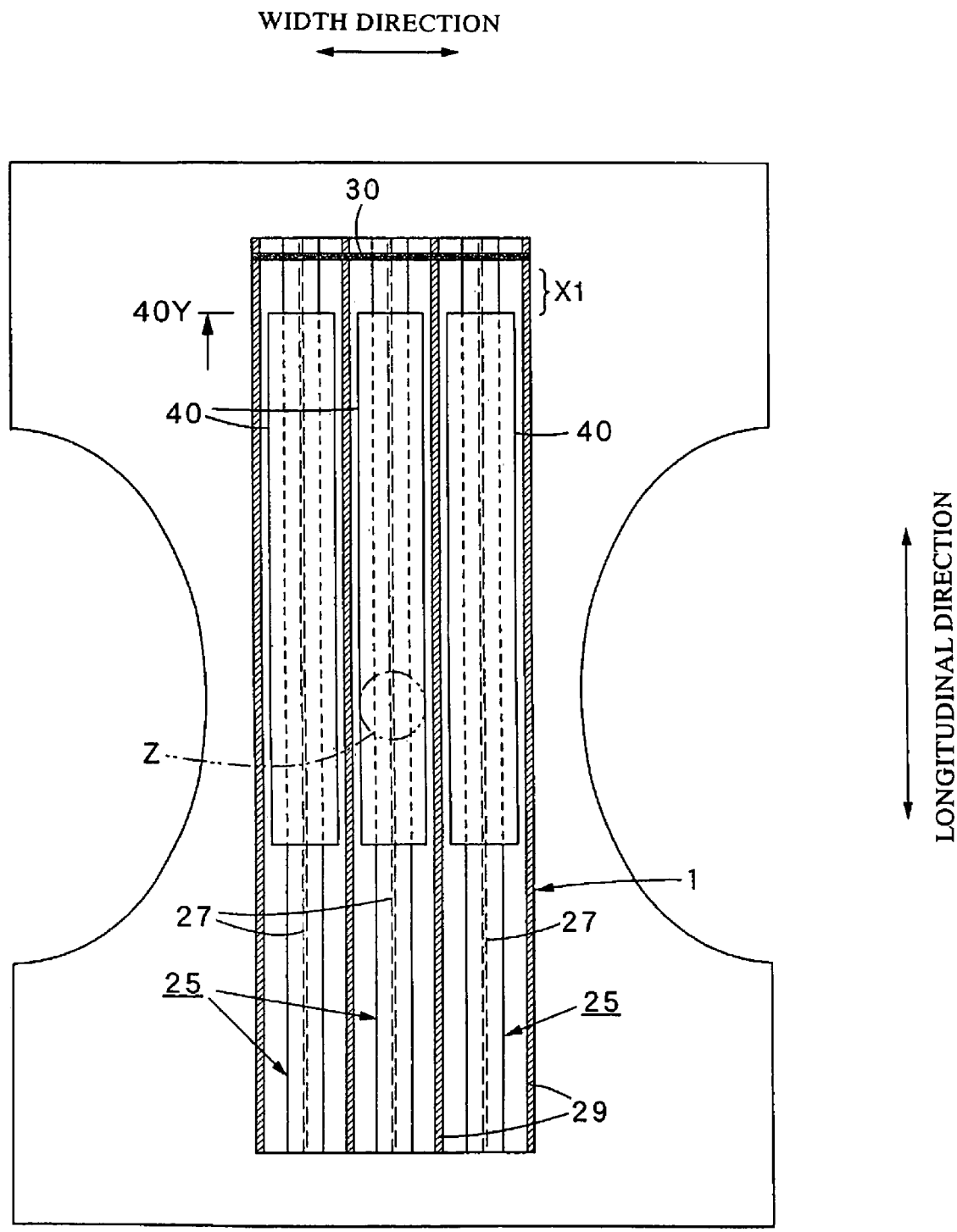
FIG. 5 is a schematic plan view that depicts arrangement of an absorbent and an absorption control layer.

As evident from comparison of FIG. 2 to FIG. 4, according to this embodiment, three absorbents 25 elongated to be generally as long as or slightly longer than the body fluid absorbent portion 1 are provided to extend from the abdomen side to the back side in the longitudinal direction of the article and aligned in the width direction of the article. The central body fluid absorbent 25 is arranged to correspond to the body liquid receiving portion Z, the absorbents 25 on both sides are arranged at positions at which they do not correspond to the body fluid receiving portion Z. In addition, only one longitudinal end 30 of each absorbent 25 is fixed to the article by an adhesive such as the hot melt adhesive, bonding means such as a heat seal or the like whereas the other end thereof is a free end. In the embodiment shown in FIGS. 1 to 4, the fixed portion 30 is provided only on the back side so as to move the absorbents 25 to the back side. Alternatively, if the absorbents 25 are to be moved to the abdomen side, the fixed portion 30 can be provided only on the abdomen side. As can be seen, the fixed portion can be provided at an arbitrary position that is a moving destination of the absorbent 25.

It is noted, however, that the number of absorbents 25 is not limited to any specific number according to the present invention. The number of absorbents may be one, two or four or more. In addition, the present invention is not limited by the arrangement of the absorbents 25. The absorbents 25 can be arranged not only in the longitudinal direction of the article but also in the width direction of the article or arranged to be inclined with respect to the longitudinal direction thereof. Further, the present invention is not limited by presence or absence of the fixed portion 30 and the absorbent 25 may not include the fixed portion 30.

The absorption control layer 40 according to this embodiment is formed by a cylindrical material entirety of which constitutes the liquid impermeable range. The absorbents 25 are inserted into an inner cavity of the absorption control layer 40 so as to be able to cover the absorbents 25 in the range in the longitudinal direction of the article including the body fluid receiving portion Z. With a view of avoiding manufacturing trouble, the absorption control member 40 is preferably temporarily bonded to surrounding members, e.g., the absorbents and a diffusion layer 50 to be described later. To this end, a water soluble (water dispersible) hot melt adhesive an adhesive power of which is lowered when absorbing the body fluid can be used.

The liquid impermeable range of the absorption control layer 40 can be appropriately defined as long as the range includes the portion corresponding to the body fluid receiving portion Z. Preferably, the liquid impermeable range is a range up to a position 40Y slightly separated from the fixed portion 30 toward the free portion 31. In the embodiment shown in the drawings, the absorption control layer 40 that is entirely liquid impermeable is provided in a range from a position generally corresponding to the anus to the position Y slightly separated from the absorption member fixed portion 30 past the hip joint. This range in the longitudinal direction of the article serves as the liquid impermeable range. To perfectly fulfill a body fluid blocking function, the liquid impermeable range preferably covers up to a free end 25f of the absorbent 25. However, if the diffusion layer 50 and a body fluid storage portion 60 to be described later are provided, it suffices to block the body fluid from the body fluid receiving portion Z to a portion near the fixed portion 30 of the absorbent 25.

As a material for the absorption control layer 40, a liquid-impermeable water-soluble material ends of which are dissolved whenever the body fluid is excreted or, more specifically, a water soluble film having an absorbent 25-side surface that is not subjected to a water-repellent treatment and an opposite surface that is subjected to the water-repellent treatment by silicon machining or fluorination. In this case, the entire absorption control layer 40 forms a continuous liquid impermeable range. The water soluble film is preferably a film that can be perfectly dissolved in 30 minutes after being immersed in a normal saline solution at 30° C. For example, a film having a trade name "Hi-Selon" manufactured by the Nippon Synthetic Chemical Industry Co., Ltd can be used for the absorption control layer 40.

Figure 6:
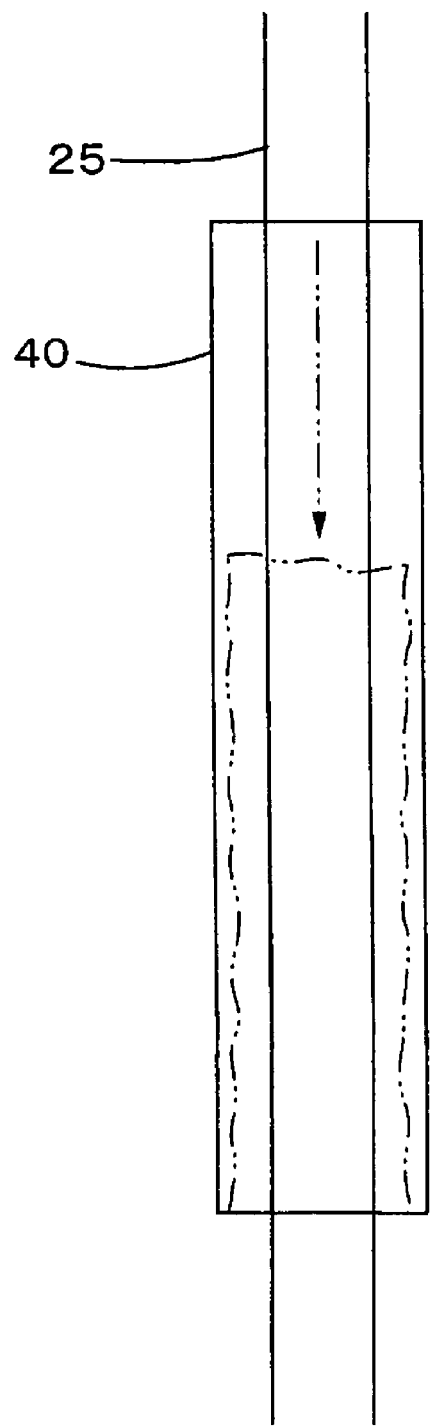
FIG. 6 is a plan view that depicts another example of the absorption control layer.

Alternatively, as shown in FIG. 6, the absorption control layer 40 can be formed using a liquid impermeable sheet that shrinks by 50% or more in area when being wet. In this case, the entire absorption control layer 40 constitutes the continuous liquid impermeable range, which is reduced by shrinkage without being dissolved. The liquid impermeable sheet that shrinks by 50% or more in area when being wet can be manufactured by forming fibers obtained by carboxymethylating denatured polyvinyl alcohol fibers or cellulose fibers (specifically, those disclosed in Japanese Patent Examined Publication No. 6-102068 and Japanese Patent No. 2656245) or the like into a nonwoven fabric, a paper, or a cloth. A shrinkage ratio of the liquid impermeable sheet 30 can be appropriately set. In this case, a shrinkage direction of the liquid impermeable sheet 31 is set to an opposite side to the fixed portion 30 of the absorbent, and an end thereof on the opposite end is fixed to the article, e.g., the surrounding members such as the leak-proof layer 3 and the like.

Figure 7:
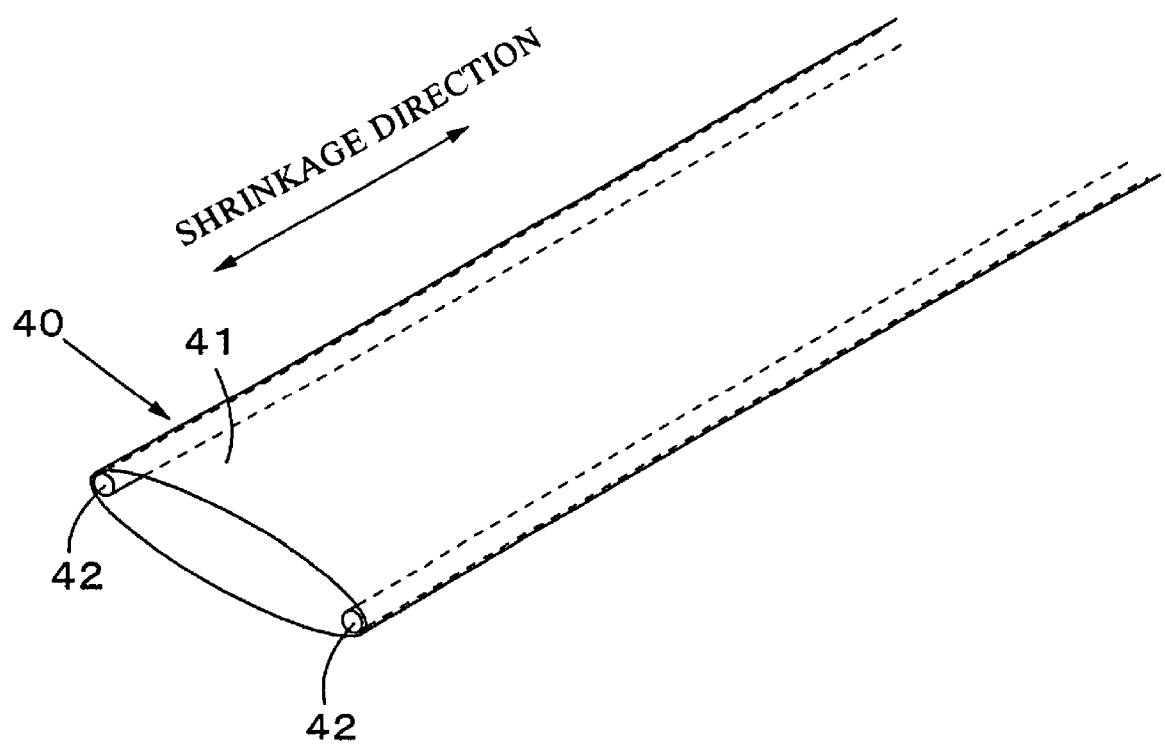
FIG. 7 is a perspective view of important parts that depicts another example of the absorption control layer.

Alternatively, as shown in FIG. 7, for example, the absorption control layer 40 can be formed by integrating the liquid impermeable sheet. 41 with a shrinkable material 42 shrinking when contacting with the body fluid. In this case, similarly to the example of FIG. 6, the entire absorption control layer 40 constitutes the continuous liquid impermeable range. In addition, a shrinkage direction of the liquid impermeable sheet 41 is set to the opposite side to the fixed portion 30 of the absorbent, and an end thereof on the opposite side is fixed to the article, e.g., surrounding members such as the leak-proof layer 3. In the example of FIG. 7, the shrinkage direction of the shrinkable material 42 is made unidirectional, so that a reduction direction of the liquid impermeable sheet 41 is made unidirectional.

As a material for the liquid impermeable sheet 41, a material that does not shrink when contacting with the body fluid such as a polyethylene sheet or a nonwoven fabric subjected to a water-repellent treatment as popular in the field of body fluid absorbent articles can be used. In addition, even if a liquid impermeable sheet that shrinks when contacting with the body fluid or the liquid impermeable sheet that is dissolved when contacting with the body fluid is used for the absorption control layer 40, the absorption control layer 40 can be formed by integrating the liquid impermeable sheet with the shrinkable material 42 if it is necessary to do so, for example, to accelerate or help reduction of the liquid impermeable range.

As a material for this shrinkable material 42, a shrinkage yarn formed by uniformly aligning a plurality of polyvinyl alcohol long fibers or a shrinkage yarn obtained by spinning cellulose short fibers, carboxymethylating the spun fibers to thereby hardening the fibers can be suitably used. Specifically, any one of yarns disclosed in Japanese Patent Examined Publication No. 6-102068 and Japanese Patent No. 2656245, and a commercially available yarn having a trade name of "Solvron Yarn®" manufactured by Nitvy Company Limited can be used 42. A thickness of the yarn is preferably 500 to 1600 dtex. As the shrinkable material 42, the shrinkage member in every form such as a filamentary form or a corded form having a circular or rectangular cross section as well as a sheet form, a film form, and a net form can be used. The shrinkable material 42 may be filamentary or spun yarn. To enable efficient shrinkage of the liquid impermeable sheet 41, it is preferable that a plurality of shrinkable materials 42 are equidistantly arranged in a longitudinal direction.

The shrinkable material 42 can be integrated with the liquid impermeable sheet 41 by bonding or welding. Alternatively, the shrinkable material 42 can be integrated therewith by, for example, sawing it on the liquid impermeable sheet 41, winding it around the sheet 41, or tangling it with the sheet 41. In this case, the shrinkable material 42 is integrated with the liquid impermeable sheet 41 so that at least both ends of the shrinkable material 41 in the shrinkage direction are not separated from the liquid impermeable sheet even when the liquid impermeable sheet contacts with the body fluid or a shrinkage tensile force acts on the sheet. Since the hot melt adhesive, in particular, is the water soluble (water dispersible) adhesive the adhesive power of which is lowered when absorbing the body fluid, the shrinkable material 42 capable of keeping a sufficient bonding strength at least on the both ends is used. The shrinkable material 42 may be exposed to either an absorbent-side surface or a surface layer 2-side surface of the liquid impermeable sheet 41. It is preferable that the shrinkable material 42 is exposed only to the absorbent-side surface thereof. The absorption control layer 10 thus configured shrinks following shrinkage of the shrinkable material 42 when the excreted body fluid contacts with the shrinkable material 42.

Figure 8:
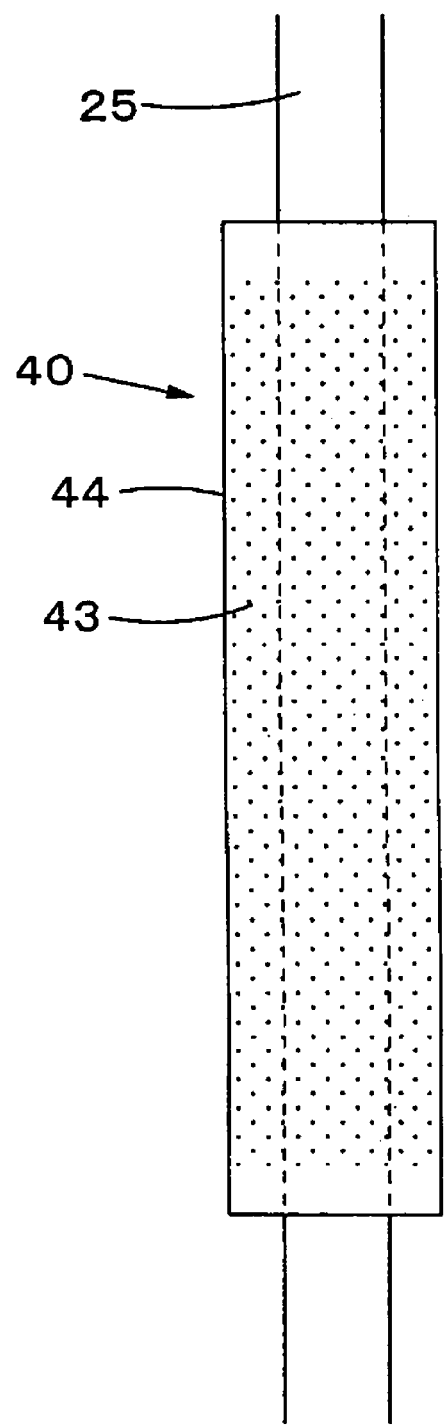
FIG. 8 is a plan view that depicts another example of the absorption control layer.

Alternatively, as shown in FIG. 8, the absorption control layer 40 can be formed using a body fluid permeable sheet 44 which is subjected to a water-repellent treatment 43 and a water repellency of which is lost when contacting with the body fluid for a predetermined time or more. The water-repellent treatment 43 can be performed on the absorbent-side surface, the opposite surface to the absorbent-side surface, both the absorbent-side surface and the opposite surface, or entirety of the sheet 44. If so, the entire absorption control layer 40 does not constitute the liquid impermeable range but a portion having the water repellency (the water-repellent part 43 before use) corresponds to the liquid impermeable range. In this case, since the more body fluid is supplied to surroundings of the water-repellent portion 43, the loss of the water repellency progresses from peripheral edges of the water-repellent portion 43 toward a center thereof.

Figure 9:
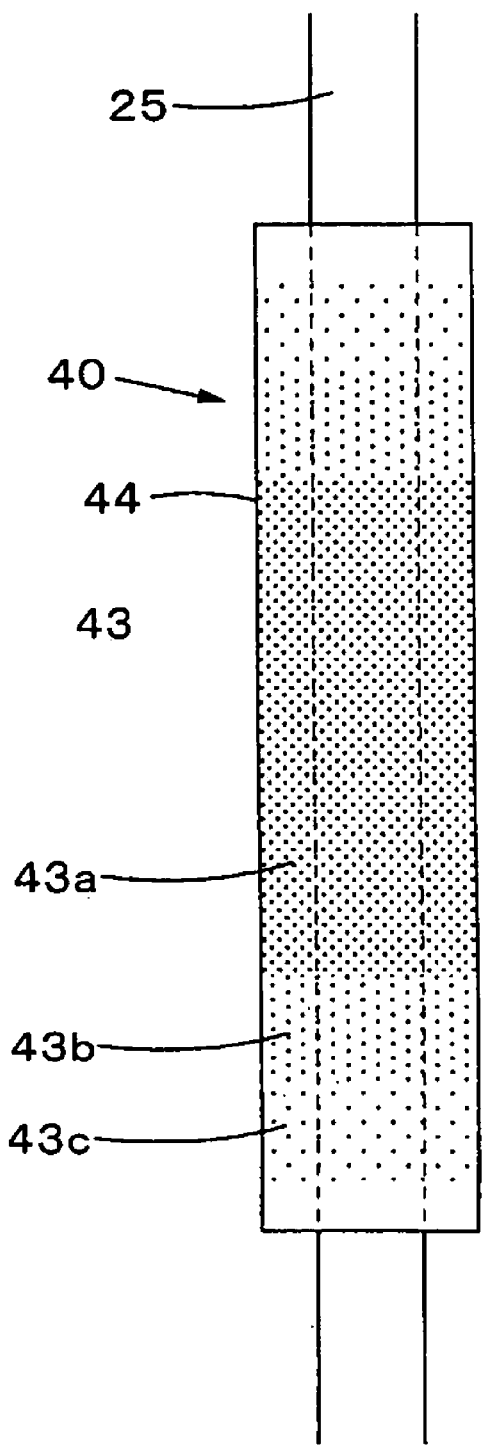
FIG. 9 is a plan view that depicts another example of the absorption control layer.

Needless to say, a degree of the water-repellent treatment can be changed according to a treatment position. As shown in FIG. 9, for example, the type and the degree of the water-repellent treatment can be changed as indicated by reference symbols 43a to 43c so that the water repellency is lost easily gradually from the center to both ends of the portion 43 in the longitudinal direction of the article.

The body fluid permeable sheet 44 which has been subjected to the water-repellent treatment and the water repellency of which is lost when contacting with the body fluid for the predetermined time or more can be manufactured by applying a solution of a mixture of a water repellent agent such as a heavy metal soap, a wax or silicon and an emulsifying and dispersing agent onto the body fluid permeable sheet such as a hydrophilic nonwoven fabric. At this time, by adjusting the emulsifying and dispersing agent, it is possible to adjust the degree of water repellency to be lost. Time in which the water repellency is lost can be appropriately set according to the type of the body fluid and the type of the article (whether the article is a baby diaper, an adult diaper, a tape stopper paper diaper, a briefs type paper diaper, a paper diaper using a pad, a daytime or nighttime paper diaper, a sanitary napkin for daytime, nighttime, or heavy bleeding day, or the like).

Figure 10:
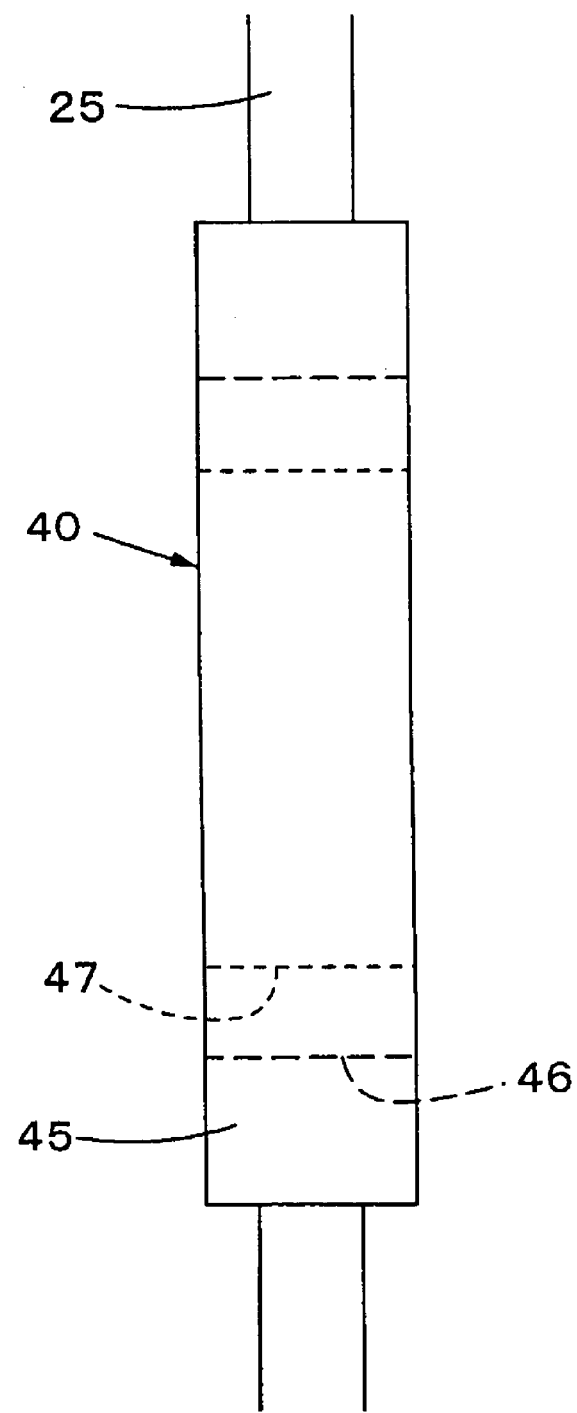
FIG. 10 is a plan view that depicts another example of the absorption control layer.

If the water soluble layer is used as the absorption control layer 40, the layer 40 is partially formed to have a multilayer structure using a plurality of water soluble layers 45 to 47 having a common solubility or different solubilities as shown in FIG. 10. It is thereby possible to change a dissolution degree (a dissolution speed and a dissolution range) according to position. In the example shown in FIG. 10, the absorption control layer 40 having a three-layer structure is provided and configured so as to have a smaller length in the longitudinal direction of the article toward the lower layer 47 of the three-layer structure. In this case, in an initial stage, since only the upper layer 45 is dissolved, the reduction of the liquid impermeable range is moved relatively speedily in a wide range. In an intermediate stage, both the upper and intermediate layers 45 and 46 are dissolved and the liquid impermeable range is then reduced, so that the speed and the range are reduced by one level. In a later stage, all of the upper, intermediate, and lower layers 45 to 47 are dissolved and the liquid impermeable range is then reduced, so that the speed and the range are further reduced.

In addition, one liquid impermeable range of the present invention may be provided per absorbent 25 as shown in the drawings. Alternatively, a plurality of liquid impermeable ranges can be provided at a plurality of locations, respectively if it is necessary to do so. If so, a plurality of absorption control layers 40 can be provided at a plurality of locations, respectively or a plurality of liquid impermeable ranges can be provided per absorption control layer 40.

If diffusibility of the body fluid is controlled according to the liquid impermeable range of the present invention, a plurality of liquid impermeable ranges are provided. By doing so, the liquid impermeability can be set different at each position according to a density of an arrangement of the ranges. For example, an arrangement in which distances between the liquid impermeable ranges are narrower as closer to the center of the layer 40 in the longitudinal direction of the article to make it more difficult for the body fluid to reach the absorbent 25 can be adopted.

In this embodiment, the body fluid diffusion layer 50 extending at least from the body fluid receiving portion Z to a fixed portion 30-side end of the free portion 31 of the absorbent 25 is provided. An extension direction of the diffusion layer 50 along the longitudinal direction of the article is substantially equal to that of the liquid impermeable range of the absorption control layer. It is, however, preferable that the diffusion layer 50 slightly protrudes to the fixed portion side of the liquid impermeable range of the absorption control layer 40. As long as the body fluid diffusion layer is provided between the surface layer 2 and the leak-proof layer 3, it may be provided between, for example, the surface layer 2 and the absorbent 5. However, since the body fluid tends to be moved toward the leak-proof layer 3 by the gravity, it is preferable to provide the layer 50 between the absorbent 25 and the leak-free layer 3. If a plurality of absorbents 25 are provided as shown in the drawings, it is preferable to independently provide a plurality of diffusion layers 50 for the respective absorbents 25. Alternatively, the diffusion layer 50 may be formed integrally with all the absorbents 25.

As a material for the body fluid diffusion layer 50, a fiber assembly (e.g., an absorbent paper) having a Klemm water absorption according to "Testing Method for Water Absorption of Paper and Paperboard by Klemm Method" specified in JIS P 8141, which absorption is 100 millimeters or more, particularly 150 millimeters or more in ten minutes is suitably used. More specifically, a fiber assembly consisting of synthetic fibers (rayon fibers or the like) surfaces of which are made hydrophilic or consisting of synthetic fibers (rayon fibers or the like) surfaces of which are made hydrophilic and cellulose fibers (pulp fibers or the like), having a basis weight of 30 to 100 g/m$^2$, particularly 30 to 50 g/m$^2$, and a Klemm water absorption of 100 millimeters or more, particularly 150 millimeters or more after ten minutes using a normal saline solution specified in JIS P 8141 can be used. It is particularly suitable to use a fiber assembly obtained by tangling a rayon fiber web by water jet, or a fiber assembly obtained by overlaying pulp fibers on a rayon fiber web and tangling them by water jet.

Further, according to this embodiment, the body fluid storage portion 60 is provided in contact with the body fluid diffusion layer 50 in the range including the body fluid receiving portion Z. The body fluid storage portion 60 is intended to temporarily store the body fluid received via the surface layer 2 and to prevent the body fluid from going backward toward the body via the surface layer 2. Due to this, the body fluid storage portion 60 may be provided at least in the body fluid receiving portion Z. Preferably, the body fluid storage portion 60 is also provided in a portion corresponding to the body fluid receiving portion Z in the width direction of the article. In the embodiment shown in the drawings, therefore, the body fluid storage portions 60 are provided in regions in which the absorbents 25 are arranged on both sides, respectively. A length of the storage portion 60 in the longitudinal direction of the article is preferably set so that there is enough room in front of and in rear of the body fluid receiving portion (e.g., in the example illustrated, a rear side of the portion 60 extends up to the hip joint part of the article).

The body fluid storage portion 60 functions to prevent the body fluid from going backward by temporarily storing the body fluid and supplying the body fluid to the outside if it is necessary to do so. The body fluid storage portion 60 can be formed of a flexible material having continuous cavities, e.g., a so-called cellulose sponge.

It is substantially essential to provide the diffusion layer 50 and the body fluid storage portion 60 in the paper diaper in which the body fluid is raised during diffusion of the body fluid or a diffusion distance is large. However, in case of the daytime sanitary napkin in which the body fluid is hardly raised and the diffusion distance is small, they can be omitted.

A material for the absorbent 25 of the present invention is not limited to a specific material as long as the material includes the body fluid absorption and holding function and the shrinkage function when contacting with the body fluid. For example, the material as disclosed in the International Publication PCT/JP02/00833 referred to in the Background Art part can be used.

Figure 11:
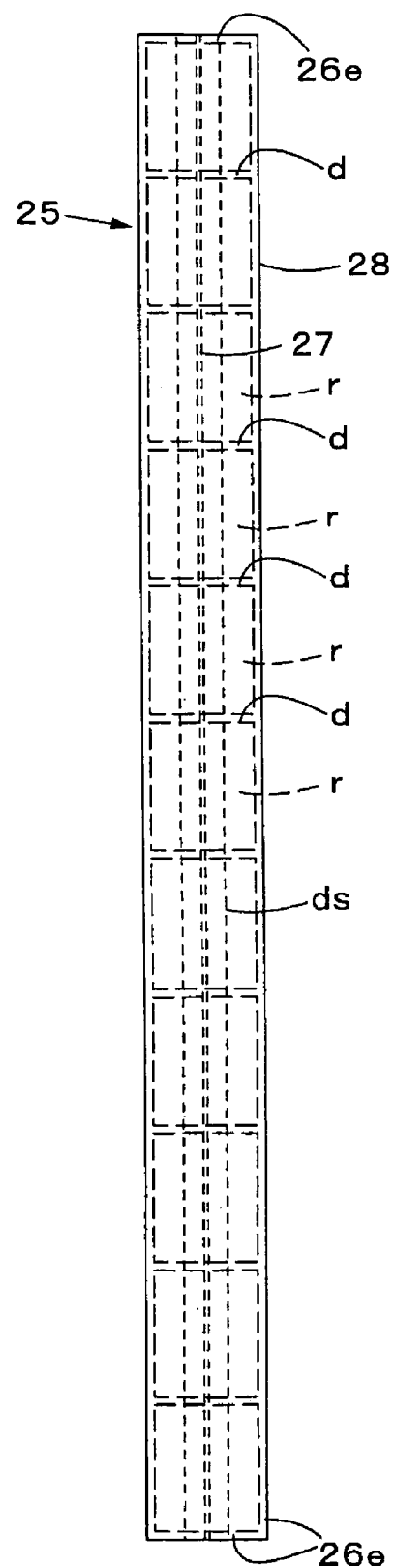
FIG. 11 is a plan view of the absorbent.
Figure 12:
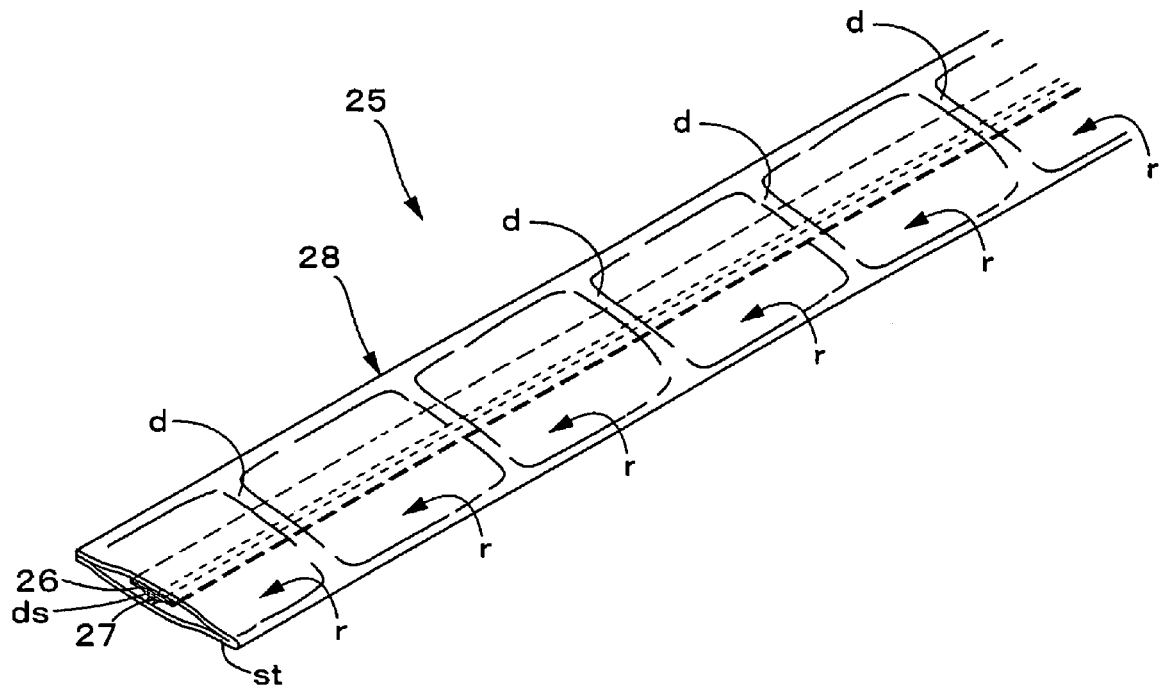
FIG. 12 is a perspective view of important parts of the absorbent.
Figure 13:
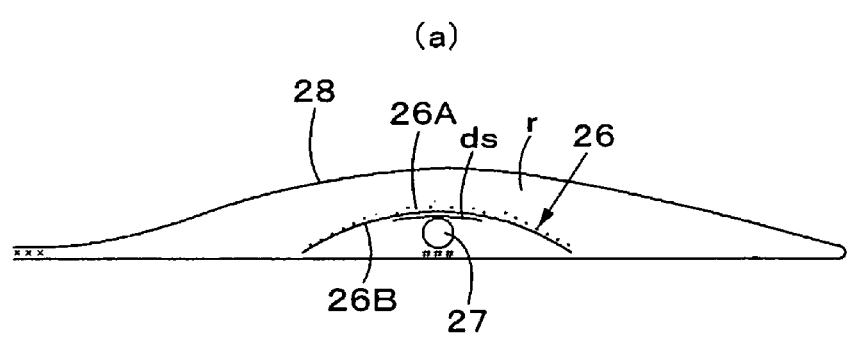
FIGS. 13(a) and 13(b) are schematic cross-sectional views of compartments for the absorbent, respectively.
Figure 13:
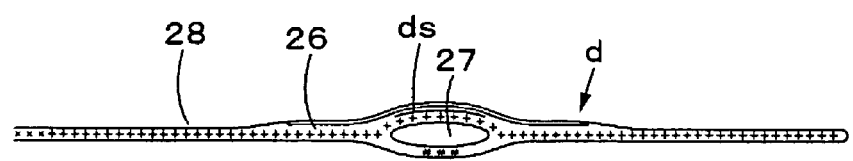

By way of example, as shown in FIGS. 11 to 13, the absorbent 25 includes, as important constituent elements, an elongated bag body 28, an elongated shrinkage member 27 attached to the bag body 28 generally entirely in a longitudinal direction thereof and shrinking when contacting with the body fluid, and an elongated body fluid absorbent member 26 arranged to spread generally entirely within the bag body 28 in the longitudinal direction thereof. The absorbent 25 that is elongated as a whole can be, therefore, used.

Particularly in the embodiment illustrated in the drawings, the absorbent 25 is provided so that a body fluid diffusion member ds comes in contact with the body fluid absorbent member 26. The body fluid diffusion member ds is intended to promote the body fluid absorbent member 26 to diffuse the body fluid and to prevent local absorption by polymers 26A. The body fluid diffusion member ds is preferably provided at and near a position corresponding to the body fluid receiving portion Z (up to a absorbent fixed portion 30-side predetermined region in the longitudinal direction of the particle, in particular). In addition, particularly if the body fluid absorbent member 26 is elongated as described in this embodiment, the body fluid diffusion member ds is preferably provided along the longitudinal direction of the member 26 and generally entirely in the longitudinal direction thereof.

Figure 15:
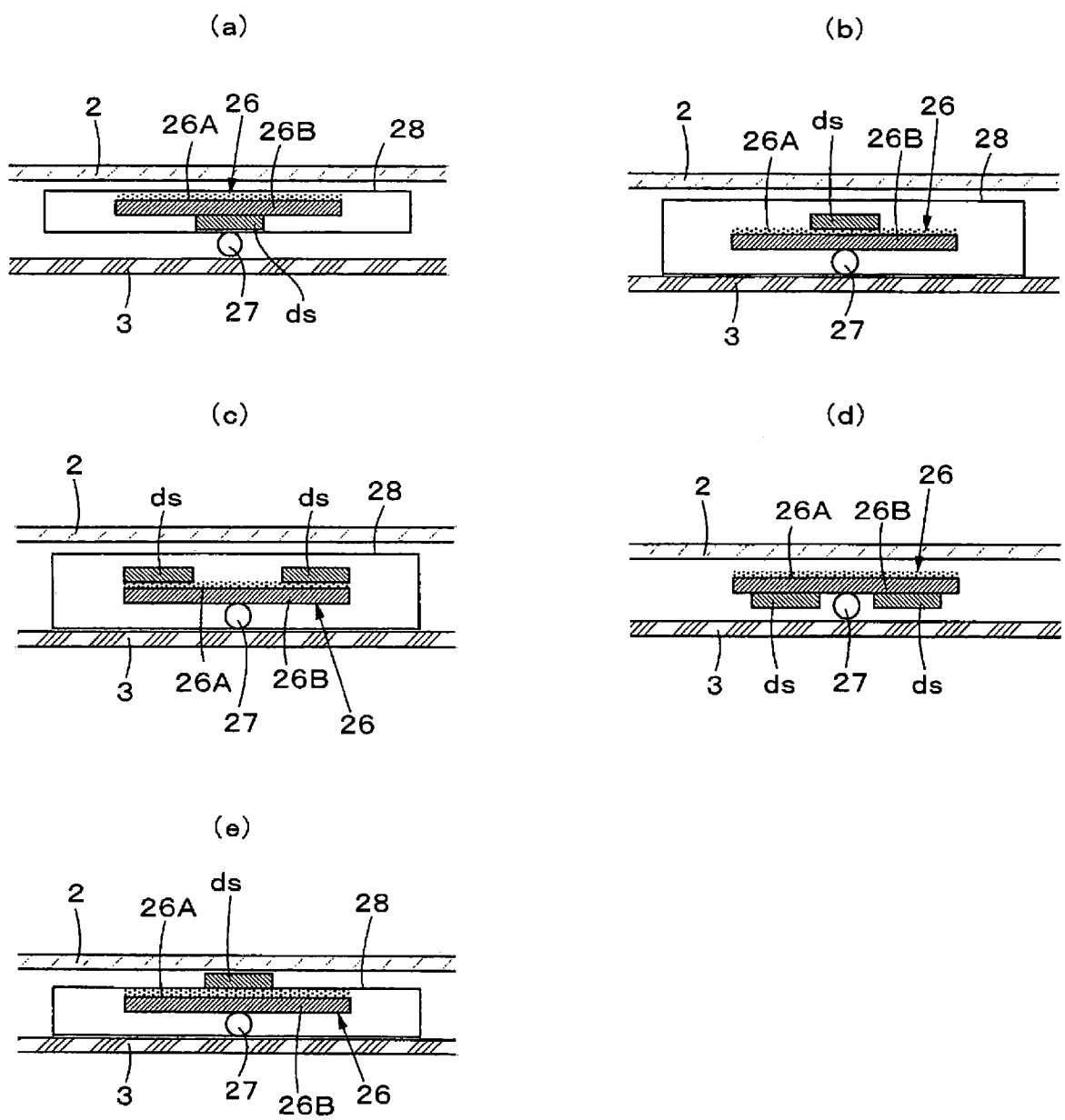
FIG. 15 is a schematic cross-sectional view that depicts various forms of the absorbent.

Further, if the shrinkage member 27 is arranged on a side surface of a back surface layer 3 within the bag body 28 and the body fluid absorbent member 26 is arranged on the surface layer 2-side thereof as shown in the absorbent 25 according to this embodiment, the body fluid diffusion member ds is preferably provided between the body fluid absorbent member 26 and the shrinkage member 27 as shown in the drawings. In this case, the body fluid diffusion member ds can accelerate supplying the body fluid to the shrinkage member 27. It is noted, however, that the body fluid diffusion member ds can be provided at an arbitrary position as long as it is provided at a position at which the member ds contacts with the body fluid absorbent member 26. FIG. 15 depicts various examples of arrangement of the body fluid diffusion member relative to the body fluid absorbent member 26. As evident from FIGS. 15(a) and 15(b), the body fluid diffusion member ds can be arranged not only on only the back surface layer 3-side of the body fluid absorbent member 26 but also only on the surface layer 2-side thereof. Further, as shown in FIGS. 15(c) and 15(d), a plurality of body fluid diffusion members ds can be provided per body fluid absorbent member 26. In this case, as shown in FIGS. 15(c) and 15(d), the body fluid diffusion members ds can be provided not only on only the surface layer 2-side or the back surface layer 3-side of the body fluid absorbent member 26 but also on both the surface layer 2-side and the back surface layer 3-side thereof, respectively, although not shown therein. In the latter case, it is preferable to give a gap between the body fluid diffusion members ds. Besides, as shown in FIG. 15, the body fluid diffusion members ds can be provided on both sides of the body fluid absorbent member 26 in the width direction thereof, respectively so that an exposed portion of the super absorbent polymer 26A or a bonded surface of the shrinkage member 27 is secured.

Needless to say, the body fluid diffusion member ds preferably comes in direct contact with the body fluid absorbent member 26. Alternatively, as shown in FIG. 15(e), the body fluid diffusion member ds can be brought into indirect contact with the body fluid absorbent member 26 via the body fluid permeable material such as the bag body 28.

The super absorbent polymers can be fixed to the body fluid diffusion member ds, in which case the body fluid diffusion member ds is not necessarily arranged to be adjacent to the body fluid absorbent member 26.

A material for the body fluid diffusion member ds is not limited to a specific one as long as spot absorption is reduced thanks to its diffusivity as compared with an instance in which the body fluid diffusion member ds is not present. For example, a fiber assembly sheet consisting of synthetic fibers (rayon fibers or the like) surfaces of which are made hydrophilic or consisting of synthetic fibers (rayon fibers or the like) surfaces of which are made hydrophilic and cellulose fibers (pulp fibers or the like), having a basis weight of 30 to 100 g/m$^2$ particularly 30 to 50 g/m$^2$, a Klemm water absorption 100 millimeters or more, particularly 150 millimeters or more after ten minutes using a normal saline solution specified in JIS P 8141, and having a water holding capacity of 6.0 g/g or more, particularly 7.0 g/g or more can be used. It is particularly suitable to use a fiber assembly obtained by tangling a rayon fiber web by water jet, or a fiber assembly obtained by overlaying pulp fibers on a rayon fiber web and tangling them by water jet.

The "water holding capacity" is measured through the following steps (1) to (5).

(1) Prepare a sample cut into a size of 110 millimeters long by 100 millimeters wide.
(2) Measure a basis weight (in grams) of the sample before water holding.
(3) Immerse the sample in a bat containing a normal saline solution for one minute.
(4) Measure a basis weight (in grams) of the sample after water holding.
(5) Take out the sample from within the normal saline solution and suspend the sample for five minutes in a position so that a longitudinal direction of the sample is along a vertical direction.
(6) Set a value obtained by dividing a difference between the weight after water holding (grams) and the weight before water holding (grams) by the weight before water holding as the water holding capacity (g/g).

Meanwhile, the bag body 28 employed in this embodiment can be also formed by overlaying two sheets and bonding peripheral edges thereof to each other. However, the bag body 28 is preferably formed as shown in the drawings for the following reason. If one band sheet st is folded in a width direction, and peripheral edges of folded parts are overlaid and bonded to each other, the bag body 28 can be manufactured more easily. A bonded state in the latter case is indicated by symbols x in FIG. 13, and the peripheral edges are bonded to each other by a heat seal, a high frequency seal or an ultrasonic seal so as not to separate them from each other when the bag body 28 contacts with the body fluid.

A material for the bag body 28 can be appropriately selected and a body fluid permeable material such as one at least partially consisting of a nonwoven fabric or a porous film can be used as the material therefor. It is particularly preferable to use a liquid permeable hydrophilic nonwoven fabric (a well-known spunbond nonwoven fabric, nonwoven fabric to which a card web is bonded, meltblown nonwoven fabric or composite nonwoven fabric thereof) containing thermoplastic synthetic fibers and having a basis weight of about 15 to 20 g/m$^2$, tissue paper containing synthetic pulp (SWP manufactured by Mitsui Chemicals, Inc. or the like) and having a basis weight of about 15 to 20 g/m$^2$ or the like. The bag body 28 is integrated with the shrinkage member 27 and a force of about 10 to 20 N is applied to a bonded region thereof in which the bag body 28 is bonded to the shrinkage member 27 when the shrinkage member 27 shrinks. It is, therefore, preferable that the bag body 28 has a wet strength enough to resist the force.

Further, the bag body 28 shown in the drawings includes many compartments r in a longitudinal direction thereof (which compartments r may be omitted, needless to say). Partitions d for partitioning these compartments r can be formed by, as shown in, for example, FIG. 13(b), bonding two inner surfaces of the bag body 28 to each other in a width direction at intervals in a longitudinal direction of the bag body 28. The bonded portions of the partitions d are indicated by symbols +. By thus bonding, the body fluid absorbent member 26 and the shrinkage member 27 are held between the inner surfaces of the bag body and fixed to the bag body 28.

To bond these partitions d, a bonding method for separating the bonded portions when the bag body 28 contacts with the body fluid is preferably adopted. Due to this, the partitions d are bonded by an adhesive the adhesive power of which is reduced when in contact with the body fluid, e.g., a water dispersible hot melt adhesive mainly consisting of polyvinyl alcohol, polyalkylene oxide or the like, starch, a water soluble adhesive consisting of carboxymethylcellulose or the like. In this case, it is preferable to make a selection of the adhesive, a selection of an adhesive area and a pattern (one of various linear patterns such as spiral, straight, and curved patterns, as well as a surface pattern, a point pattern, and the like), and the like so that the bonding strength during contact with the body fluid is twice or more as high as that during non-contact with the body fluid.

In this case, if the partitions d of the absorbent 25 contact with the body fluid, the partitions d bonded to one another are separated and the shrinkage member fixed to the bag body 28 by bonding of the partitions d is separated therefrom. Accordingly, the super absorbent polymers 26A within the compartment r can expand to exceed an initial volume of the compartment, thereby making it more difficult to cause the so-called gel blocking. In addition, the shrinkage member 27 can freely shrink without constraint from the bag body 28 in a portion in which the shrinkage member 27 is separated from the bag body 28. At this time, since the region of the shrinkage member 27 which is out of contact with the body fluid is not separated from the bag body 28, it is possible to ensure shrinking the absorbent 25 following shrinking of the shrinkage member 27.

It is noted, however, if this separable configuration is adopted, it is necessary to fix the shrinkage member 27 to the bag body 28 by a stronger force than the shrinking force of the shrinkage member 27 at least on both longitudinal ends of a shrinkage range (which ends correspond to the both longitudinal ends on the body fluid receiving portion Z-side fixed portion 30 of the absorbent 25 according to this embodiment). To do so, according to this embodiment, the both ends of the shrinkage member 27 are held between sheets on longitudinal both ends 26e of the bag body 28, and the sheets are bonded to each other with the shrinkage member 27 held therebetween by a heat seal, an ultrasonic seal or the like so as not to separate them when in contact with the body fluid. As a result, the both longitudinal ends of the shrinkage member 27 are not separated from those of the bag body 28 even if they contact with the body fluid.

Alternatively, not only the shrinkage member 27 can be intermittently fixed to the bag body 28 by the partitions d but also the other regions or the entire longitudinal portions of the shrinkage member 27 can be fixed to the inner surfaces of the bag body 28 by the hot melt adhesive or the like if it is necessary to do so. In case of the latter fixing, it is preferable that the fixed portions of the shrinkage member 27 are separated from the inner surfaces of the bag body 28 when contacting with the body fluid. However, they may be separated therefrom. These fixed portions are indicated by symbol # in FIG. 13.

Figure 14:
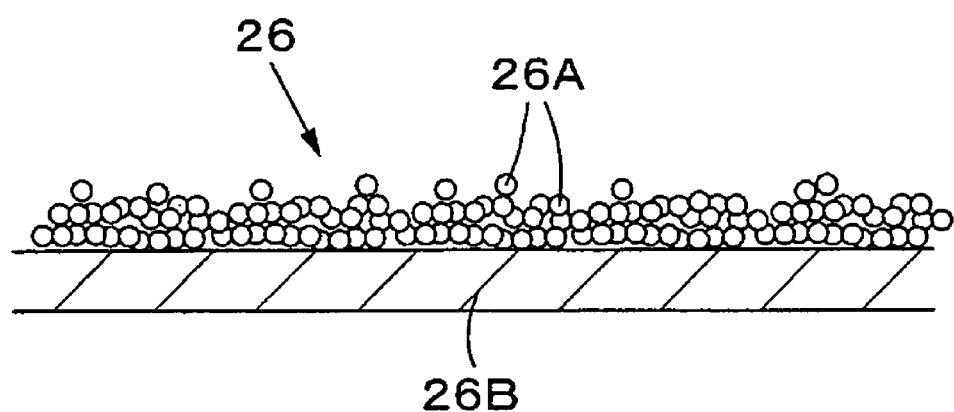
FIG. 14 is an enlarged cross-sectional view that schematically depicts a body fluid absorbent member.
Figure 14:
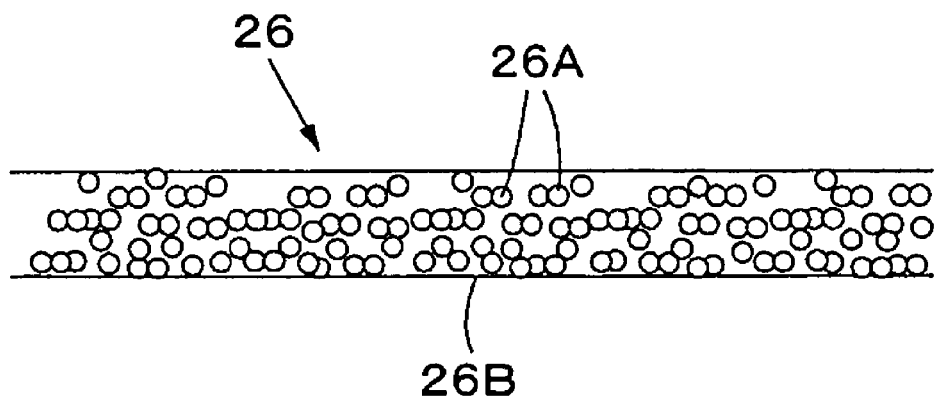

As the body fluid absorbent member 26, a member configured so that the super absorbent polymers 26A are held on a ribbon carrier 26B can be suitably used. In this case, as shown in FIG. 14(a), the polymers 26A can be held on an outer surface of the carrier 26B or, as shown in FIG. 14(b), the carrier 26B consisting of a bulky fiber assembly sheet can be used and the polymers 26A can be held between fibers within the carrier 26B. In the former case, the polymers 26A are preferably arranged on at least the surface layer 2-side outer surface of the carrier 26B. Further, a sheet absorbent member configured so that the fiber outer surface of the carrier is coated with a super absorbent polymer layer can be used as the body fluid absorbent member 26. This sheet absorbent member can be manufactured by impregnating the fiber assembly sheet with a monomer liquid and polymerizing the monomer liquid on the fiber surface by UV radiation or the like.

To make the polymers 26A held on the outer surface of the carrier 26B, the polymers 26A can be bonded onto the outer surface by the hot melt adhesive or the like. Alternatively, moisture can be applied to the polymers 26A, thereby applying an adhesive strength to bond the polymers 26A to the outer surface of the carrier 26B. To make the polymers 26A held between the fibers within the carrier 26B, they can be done so by bonding or adhesion. Alternatively, the polymers 26A may be simply tangled with the fibers mechanically. Further, depending on situations, the polymers 26A may be simply bonded without using any of these holding means. In any case, the super absorbent polymers 26A are held by the carrier at least until the manufacturing of the absorbent is completed, preferably while the product is used until it swells by the body fluid.

As the carrier 26B, a nonwoven fabric sheet that can be either hydrophilic or hydrophobic, preferably hydrophilic can be used. More preferably, a nonwoven fabric sheet consisting of hydrophilic fibers (that are preferably either synthetic fibers surfaces of which are made hydrophilic or consisting of synthetic fibers surfaces of which are made hydrophilic and cellulose fibers) having a density of 0.05 to 0.1 g/cm$^3$ and a basis weight of 30 to 100 g/m$^2$ is used as the carrier 26B.

If the polymers 26A are held within the carrier 26B, a nonwoven fabric sheet consisting of a bulky fiber assembly, more specifically, hydrophilic fibers having a density of 0.03 to 0.08 g/cm$^3$ and a basis weight of 20 to 50 g/m$^2$ can be preferably used.

As the super absorbent polymer 26A, a polymer that absorbs and holds the body fluid by a weight 20 times or more, for example, as large as its self weight and that is used in the disposable absorbent article of this type can be used. Examples of this include a starch polymer, a cellulose polymer, and a synthetic polymer. More specifically, they include a starch-acrylic acid (acrylate) graft copolymer, a saponified starch-acrylonitrile graft copolymer, a cross-linker of sodium carboxymethylcellulose, and an acrylic acid (acrylate) polymer.

An absorbing capacity of the super absorbent polymer 26A is preferably such that the polymer absorbs the body fluid by a weight ten times or more as large as its self weight in ten seconds and swells. The super absorbent polymer 26A is a powder polymer as normally used at present, or can be replaced by or used together with a fibrous polymer. The fibrous super absorbent polymer can be used by forming the polymer into a yarn or strip polymer.

An amount of the super absorbent polymers 26A by which the polymers 26A are held on the carrier 26B is determined by setting an absorption amount of the absorbent article. In this embodiment, the effect of the absorption control layer makes it difficult to cause the gel blocking resulting from the spot absorption in the body fluid receiving portion. It is, therefore, possible to hold a large amount of super absorbent polymers 26A, specifically, by 300 grams per unit area (m$^2$) of the carrier within the bag body 28.

The body fluid absorbent member thus formed can be arranged in the bag body 28 without fixing it to the bag body 28 as shown in the drawings or fixed to the inner surfaces of the bag body 28 or to the shrinkage member 27. If the shrinkage member 27 is arranged in the bag body 28 as shown in the drawings, the body fluid absorbent member 26 is preferably arranged therein while bringing the member 27 in contact with the shrinkage member 27. It is particularly preferable to arrange the shrinkage member 27 in a lower portion of one inner surface of the bag body 28, arrange the body fluid absorbent member 26 on the shrinkage member 27, and hold the shrinkage member 27 between the inner surface of the bag body 28 and the body fluid absorbent member 26.

Further, the body fluid absorbent member can be arranged to be continuous in the longitudinal direction of the absorbent 25 as shown in the drawings. Alternatively, a plurality of short body fluid absorbent members 26 can be arranged to be coupled to one another or intermittently. If the bag body includes a plurality of compartments r as described in the above example, in particular, the body fluid absorbent members 26 can be arranged in the respective compartments independently of one another. Further, the number of body fluid absorbent members 26 is not limited to one per bag body but may be two or more.

As a material for the shrinkage member 27 that generates the shrinkage force of the absorbent 25, the same material as that for the absorption control layer 40 can be used. To enable efficient movement of the absorbent 25, it is preferable to provide one or more shrinkage members 25 each having a shrinkage force of 10 N or more during absorption of the body fluid per absorbent 25.

To manufacture the absorbent 25, the following method or the like can be adopted. The body fluid absorbent member 26 having the super absorbent polymers 26A held on the carrier 26B is obtained, the shrinkage member 27 and the body fluid absorbent member 26 are arranged on a bag body formation sheet, the sheet is folded to bond peripheral edges of folded parts or a different sheet is overlaid on the sheet to bond the peripheral edges thereof to each other, and then the shrinkage member 27 is fixed to the outer surface of the bag body.

Figure 16:
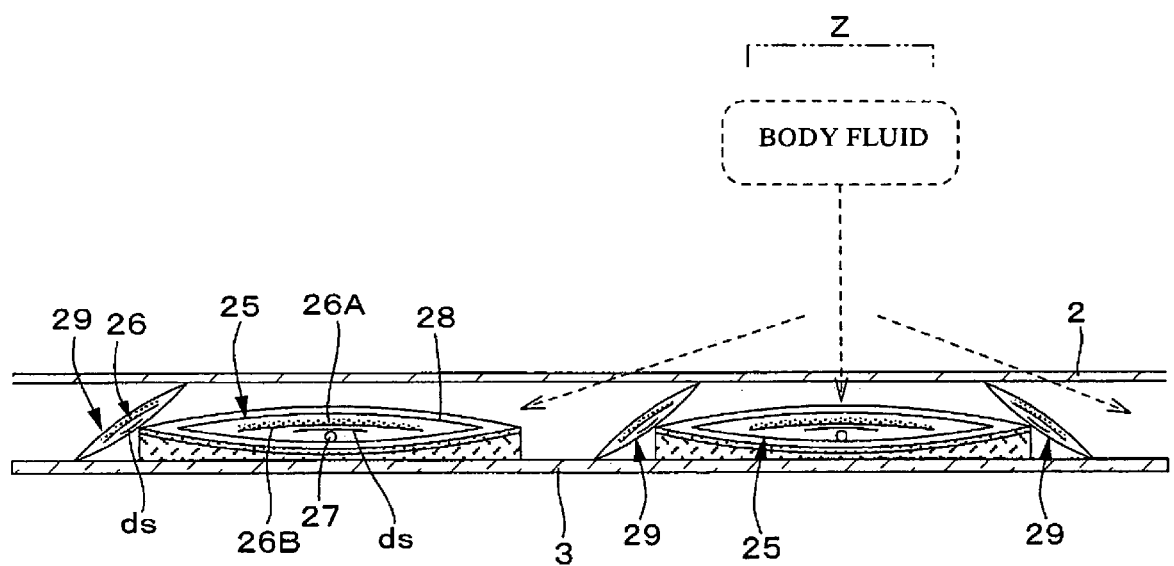
FIG. 16 is an enlarged longitudinal sectional view of important parts.

Furthermore, according to this embodiment, as shown in FIG. 16, with a view of securing a space mainly for movement of the absorbent 25 (which space also serves as an absorption control member movement space if the liquid impermeable range is reduced by shrinkage of the absorption control member), wall members 29 that extend in the longitudinal direction of the article similarly to the absorbent 25 but that are more than the absorbent 25 by one are provided within the body fluid absorbent portion 1, specifically between the surface layer 2 and the leak-proof layer 3 at larger intervals than the width of the absorbent 25, and the absorbents 25 are arranged between the wall members 29, respectively. Needless to say, the wall members 29 may not be always provided according to the present invention.

To secure the movement space for the absorbent 25, the wall members 29 are preferably fixedly bonded within the body fluid absorbent portion 1 by the hot melt, the heat seal or the like; otherwise, the wall members 29 can be simply mounted within the portion 1 without fixing them.

The wall member 29 may be a simple fiber assembly, a sponge body or the like. Preferably, the wall member 29 formed by removing the shrinkage member 27 from the absorbent 25, that is, by filling the body fluid absorbent member 26 and the body fluid diffusion member ds in contact with the member 26 into a closed bag body consisting of a body fluid permeable sheet is used. A form of the wall member 29 can be appropriately set. However, considering that the absorbent 25 is arranged between the wall members 29, the wall member 29 is preferably elongated and thin as shown in the drawings. If so, the wall member 29 can be provided in a state of falling down. It is also preferable that an arrangement position (a longitudinal position in the drawings) of the body fluid diffusion member and that of the absorbent 25 between the wall members 29 correspond to each other. Further, between the wall members 29, the body fluid diffusion member ds can be arbitrarily arranged relative to the body fluid absorbent member 26. For example, the body fluid diffusion member ds can be arranged at a center of the body fluid absorbent member 26 in the width direction of the article, arranged only outside the body fluid absorbent member 26 in the width direction of the article, arranged both inside and outside the body fluid absorbent member 26, or a plurality of body fluid diffusion members ds can be provided per body fluid absorbent member 26 (not shown).

The other constituent elements of the absorbent 25 are the same as those of the absorbent 25 stated above including modifications and denoted by the same reference symbols. They will not be, therefore, described herein.

In the paper diaper configured as stated so far, if a first excretion occurs in a non-absorbing state, the body fluid passing through the surface layer 2 is blocked by the liquid impermeable range of the absorption control layer 50. In addition, in the body fluid receiving portion Z, the body fluid is not supplied to the absorbent 25 but diffused around the absorbent 25. In this embodiment, the body fluid storage portion 60 and the body fluid diffusion layer 50 are provided. Due to this, the body fluid permeated by the surface layer 2 is temporarily absorbed and held by the storage portion 60 and diffused from the storage portion 60 toward the fixed portion 30 of the absorbent 25 via the body fluid diffusion layer 50. This body fluid is raised through the body fluid diffusion layer 50 and supplied preferentially to a region X1 of the free portion 31 of the absorbent 25 in which region the liquid impermeable range does not block the body fluid.

Figure 17:
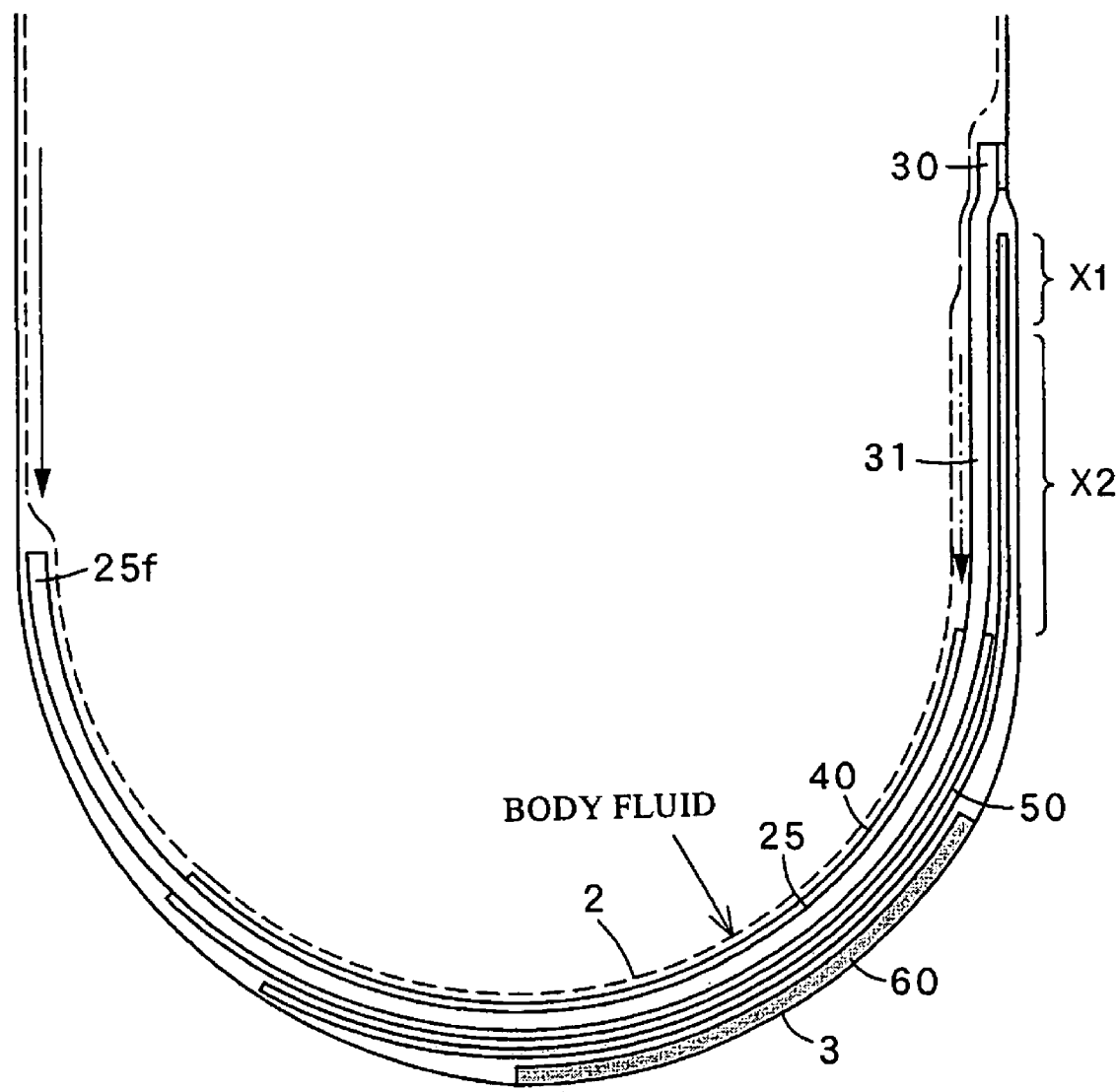
FIG. 17 is a schematic longitudinal sectional view that depicts a state after a first excretion and before a second excretion.
Figure 19:
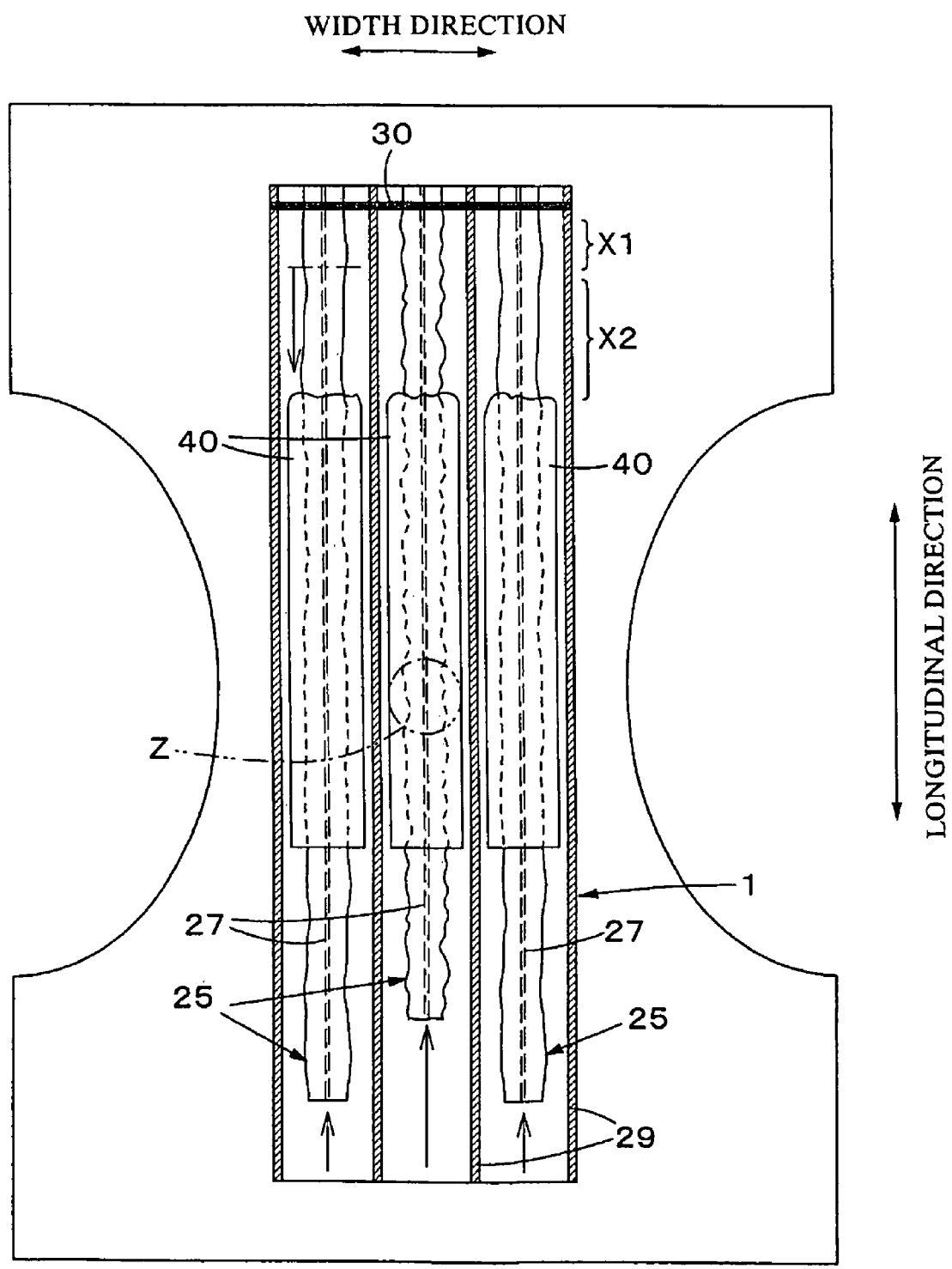
FIG. 19 is a plan view that depicts a state after the first excretion and before the second excretion.

As a result, as shown in FIGS. 17 and 19, the absorbent 25 absorbs the body fluid and shrinks. As indicated by each arrow, a non-shrinking part of the absorbent 25 is moved toward the fixed portion 30-side. Taking the absorbent shown in FIG. 11 and the like as an example, the body fluid supplied to the absorbent 25 is absorbed and held by the super absorbent polymers 26A and a part of the body fluid contacts with the shrinkage member 27, whereby a contact part of the shrinkage member 27 shrinks. As a result, the absorbent with which the shrinkage member is integrated shrinks. In this embodiment, since one end 30 of each absorbent 25 is fixed, the fixed portion 30-side absorbent 25 shrinks and a region of the absorbent-25 which previously absorbs the body fluid is moved toward the fixed side 30. Due to this, a new region of the absorbent 25 is located at a position at which the moved region is originally present. Namely, the absorbent portion of the absorbent 25 is updated relative to the body fluid supply region X1 whenever the excretion occurs.

Furthermore, after several time passes since the cylindrical absorption control layer 40 contacts with the body fluid, the liquid impermeable range thereof is reduced from the fixed portion 30 side of the absorbent 25 to the opposite side thereof. More specifically, if the absorption control layer 40 consists of the water soluble film only the surface opposite to the absorbent 25 side of which is subjected to the water repellent treatment, then the absorbent-side surface of the layer 40 which surface is not subjected to the water repellent treatment also contacts with the body fluid, and the absorbent fixed portion 30-side end of the absorption control layer 40 is dissolved. As a result, the liquid impermeable range of the layer 40 is reduced from the absorbent fixed portion 30-side to the opposite side. If the absorption control layer 40 is shrinkable, the layer 40 shrinks and moves toward the opposite side to the absorbent fixed portion 30-side. As a result, the liquid impermeable range is reduced from the fixed portion 30 side to the opposite side. If the absorption control layer 40 is the body fluid permeable sheet which is subjected to the water repellent treatment and the water repellency of which is lost when contacting with the body fluid for the predetermined time or more, the body fluid supply position X1 for supplying the body fluid to the absorbent 25, i.e., the absorbent fixed portion 30-side layer 40 more contacts with the body fluid. The water repellency on absorbent fixed portion 30-side end of the layer 40 is lost and the liquid permeable part increases thereon. As a result, the liquid impermeable range is reduced from the absorbent fixed portion 30-side to the opposite side.

Thus, because of the shrinkage and movement of the absorbent 25 and the reduction in the liquid impermeable range of the absorption control layer 40, the body fluid is not blocked by the liquid impermeable range in the new region X2 of the absorbent 25. This new region X2 of the absorbent 25 is a region in which the body fluid is originally blocked by the liquid impermeable range of the absorption control layer 40, so that the region either does not absorb the body fluid yet or has sufficiently surplus absorbing force.

During a second and the following excretions, similarly to the first excretion, the absorbent 25 is moved and the liquid impermeable range of the absorption control layer 40 is reduced step by step. Finally, the body fluid is not blocked by the liquid impermeable range even in the absorbent 25 in the body fluid receiving portion Z. In this embodiment, it is preferable that at least during the first excretion, the body fluid is not supplied to the absorbent 25 in the body fluid receiving portion Z, and that during the second and the following excretions, the body fluid is supplied to the absorbent 25 in the body fluid receiving portion Z. During the second and the following excretions, the following manner can be adopted, for example.

Figure 18:
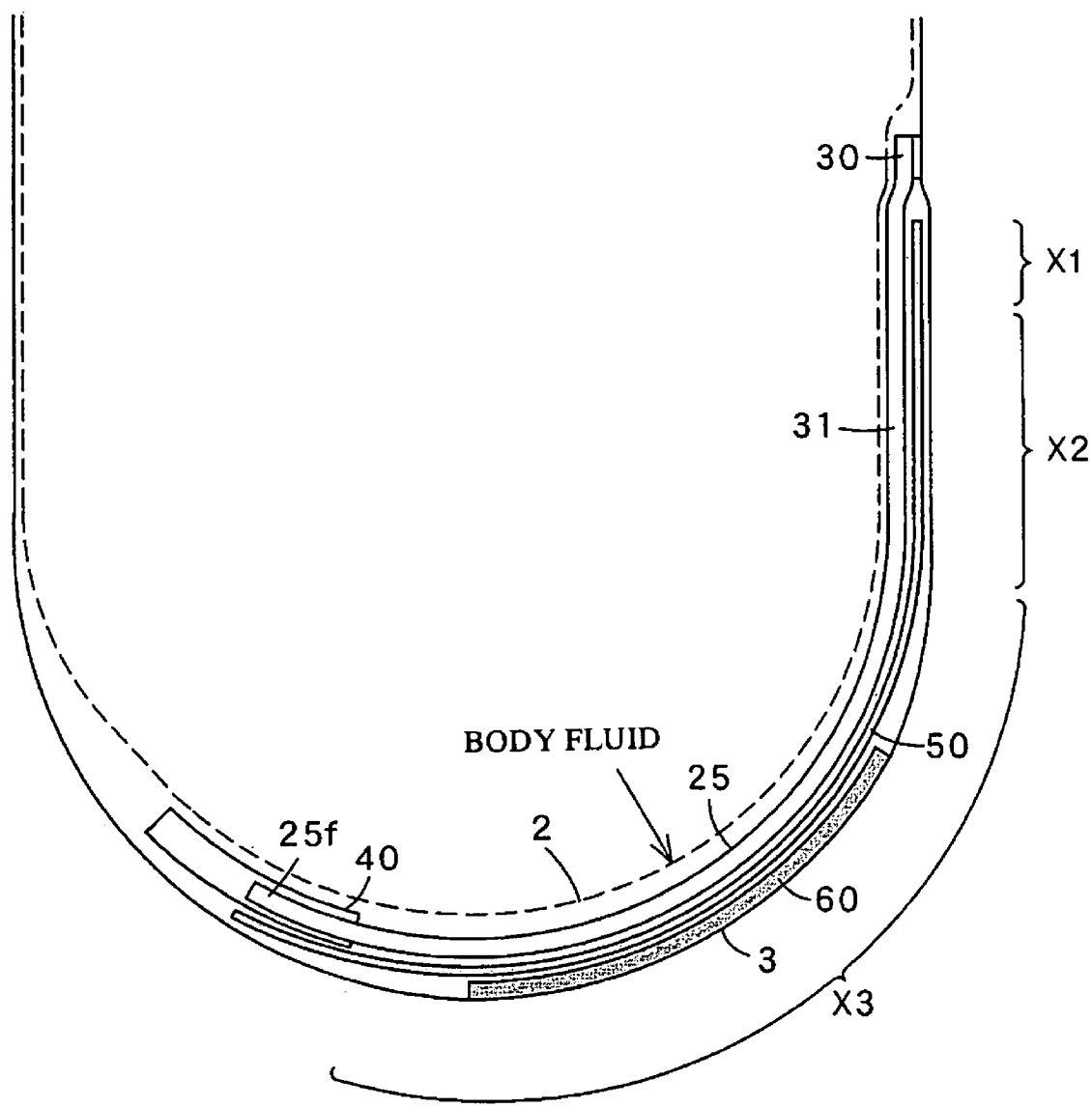
FIG. 18 is a schematic longitudinal sectional view that depicts a state after the second excretion and before a third excretion.

During the second excretion, the body fluid passing through the surface layer 2 is blocked by the liquid impermeable range of the absorption control layer 40. In the body fluid receiving portion Z, the body fluid is not supplied to the absorbent 25 but temporarily absorbed and held by the storage portion 60. The body fluid is raised from the storage portion 60 through the body fluid diffusion layer 50, and supplied to the free portion X2 of the absorbent 25 in which the body fluid is not blocked by the liquid impermeable range as a result of the first excretion. Since the position of the absorbent 25 at which the body fluid is mainly absorbed is changed over to the free end 25 f-side whenever an excretion occurs. Due to this, the body fluid is absorbed the second time while it is not influenced by the first body fluid absorption. During this second excretion, similarly to the first excretion, the absorbent 25 absorbs the body fluid and shrinks, the non-shrinking part of the absorbent 25 is moved toward the fixed portion 30-side, the liquid impermeable range of the cylindrical absorption control layer 40 is reduced from the absorbent fixed portion 30-side to the opposite side thereto. As a result, as shown in FIG. 18, the body fluid is not blocked by the liquid impermeable range in a new region X3 of the absorbent 25 including the body fluid receiving portion Z. During the next or third excretion, the body fluid is absorbed by the absorbent 25 in the body fluid receiving portion Z.

As can be seen, the absorbent 25 absorbs the body fluid preferentially in an arbitrary region due to the presence of the liquid impermeable range of the absorption control layer 40, and shrinks. Besides, this preferential absorbent region is sequentially changed over from the fixed portion 30-side to the position at which the absorbent 25 does not absorb the body fluid yet or has the surplus absorbing force by the reduction in the liquid impermeable range as indicated by reference symbols X1 to X3. It is possible to make effective use of the entire absorbent 25 and improve moving efficiency. Accordingly, the wearer can comfortably wear the paper diaper for a long time.

Moreover, as shown in the drawings, if the diffusion layer 50 and the storage portion 60 are provided between the surface layer 2 and the absorbent 25, the body fluid is diffused, moved promptly, and permeated instantaneously by the surface layer 2 and most of the body fluid that passing through the surface layer 2 is temporarily stored by the storage portion 60. Thereafter, the body fluid is diffused through the diffusion layer 5. Due to this, although it takes some time for the absorbent 25 to absorb the body fluid because of the presence of the liquid impermeable range, the body fluid hardly goes backward toward the body-side surface layer 2.

Further, if the absorbent 25 and the absorption control layer 40 are arranged between the wall members 29 as described in this embodiment, then these wall members 29 receive a pressure applied from the side that faces the body skin, and a shrinking space for the absorbent 25 and a body fluid distribution channel are secured. It is, therefore, possible to surely and efficiently update the absorbent 25 and efficiently absorb the body fluid.

According to this embodiment, in particular, the body fluid permitted by the surface layer 2 and reaching the interior of the body fluid absorbent portion 1 is not promptly absorbed by the absorbent 25 due to the presence of the liquid impermeable range of the absorption control layer 40. It is considerably advantageous to secure such a body fluid distribution channel.

If the liquid impermeable range is reduced by the shrinking of the absorption control layer 40, a space for the shrinking is also secured by the wall members 29.

Further, in this case, the wall members 29 suppress the diffusion of the body fluid in a traversing direction whether the wall members 29 are liquid permeable or liquid impermeable, thereby accelerating the diffusion along the wall members 29. Accordingly, it is also advantageous to secure the body fluid distribution channel in that the certainty and efficiency of the distribution of the body fluid to the fixed portion 30 are improved irrespective of the position of the fixed portion 30 of the absorbent 25.

Other Embodiments in Relation to Absorption Control Layer

The absorption control layer 40 according to the previous embodiment is formed by the cylindrical material entirety of which constitutes the liquid impermeable range. In addition, the absorbent 25 is inserted into the inner cavity of the absorption control layer 40 so as to be able to cover the absorbent 25 in the range in the longitudinal direction of the article including the body fluid receiving portion Z. However, the present invention is not limited to this embodiment.

Figure 20:
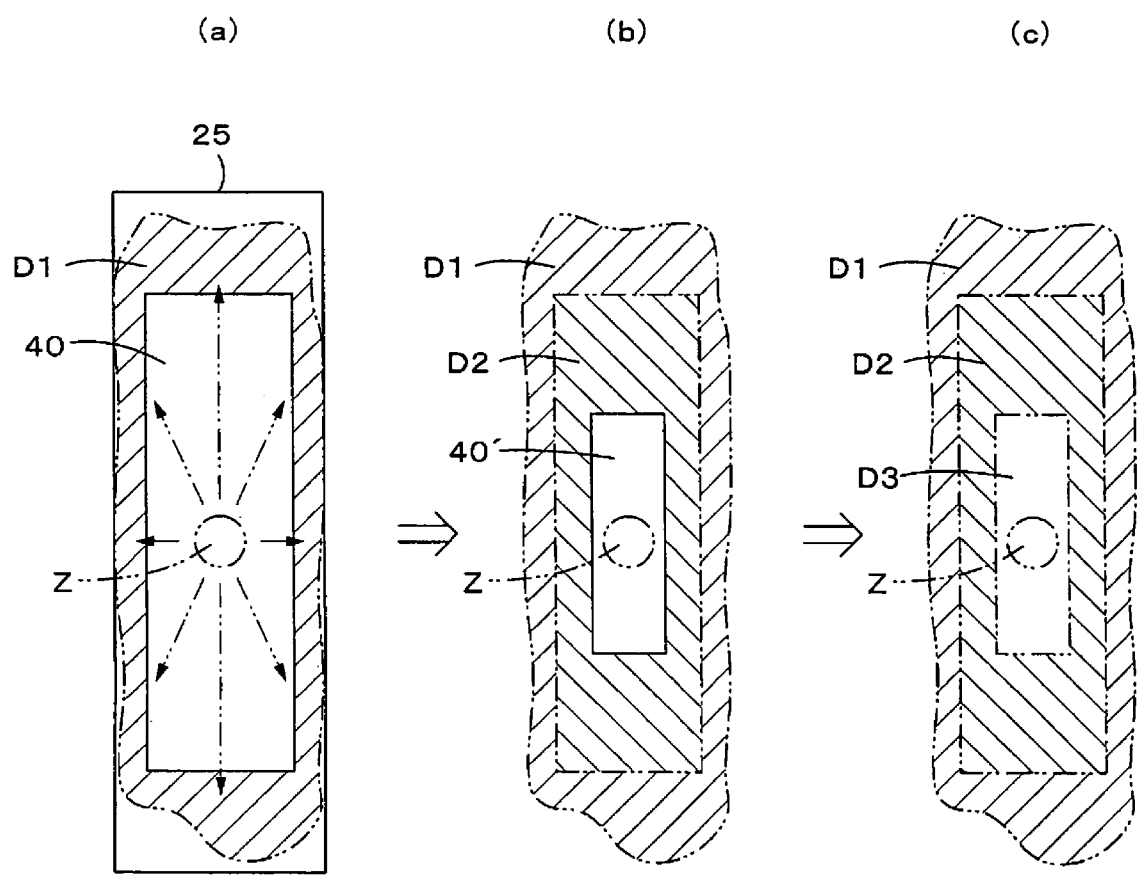
FIG. 20 is a plan view that depicts important parts (an absorbent member and a control layer) of another embodiment of the absorption control layer.
Figure 21:
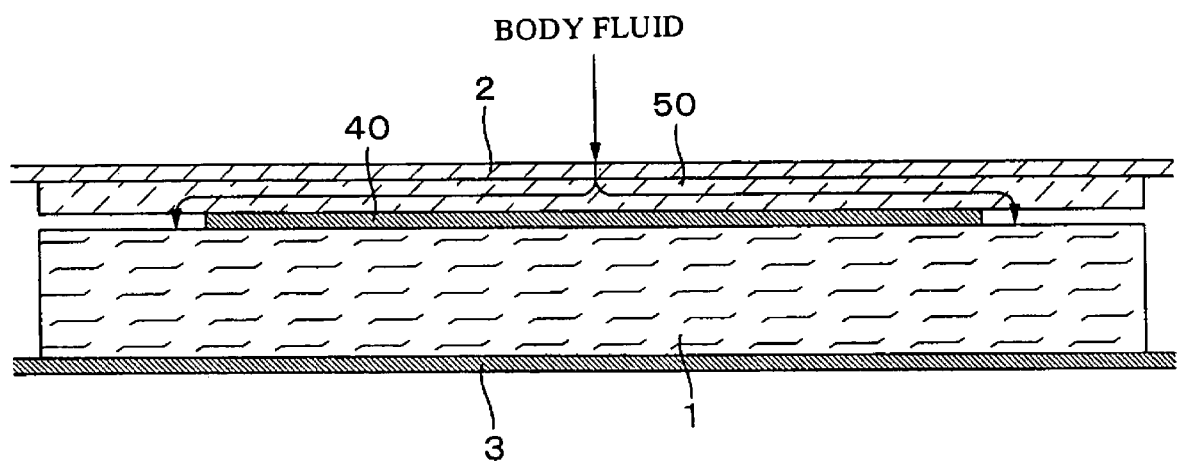
FIG. 21 is a cross-sectional view that depicts the important parts (the absorbent member and the control layer) of another embodiment of the absorption control layer.

As shown in FIGS. 20 and 21, for example, a substantially flat absorption control layer 40 can be provided to cover the absorbent 25. This flat absorption control layer 40 can be configured basically similarly to the cylindrical absorption control layer 40 stated above except that the layer 40 is flat.

The flat absorption control layer 40 can be formed by a water soluble layer dissolution of which sequentially progresses from peripheral edges to a center thereof. This water soluble layer 40 can consist of, for example, a water soluble film a surface layer 2-side surface of which is subjected to the water repellent treatment by silicon machining or fluorination and a leak-proof layer 3-side surface of which is not subjected to the water repellent treatment. In this case, the entire film forms the liquid impermeable range (therefore, a common reference symbol to the absorption control layer and the liquid impermeable range is sometimes used to denote them). Specific examples of the water soluble film are the same as those described in relation to the cylindrical absorption control layer 40.

Figure 22:
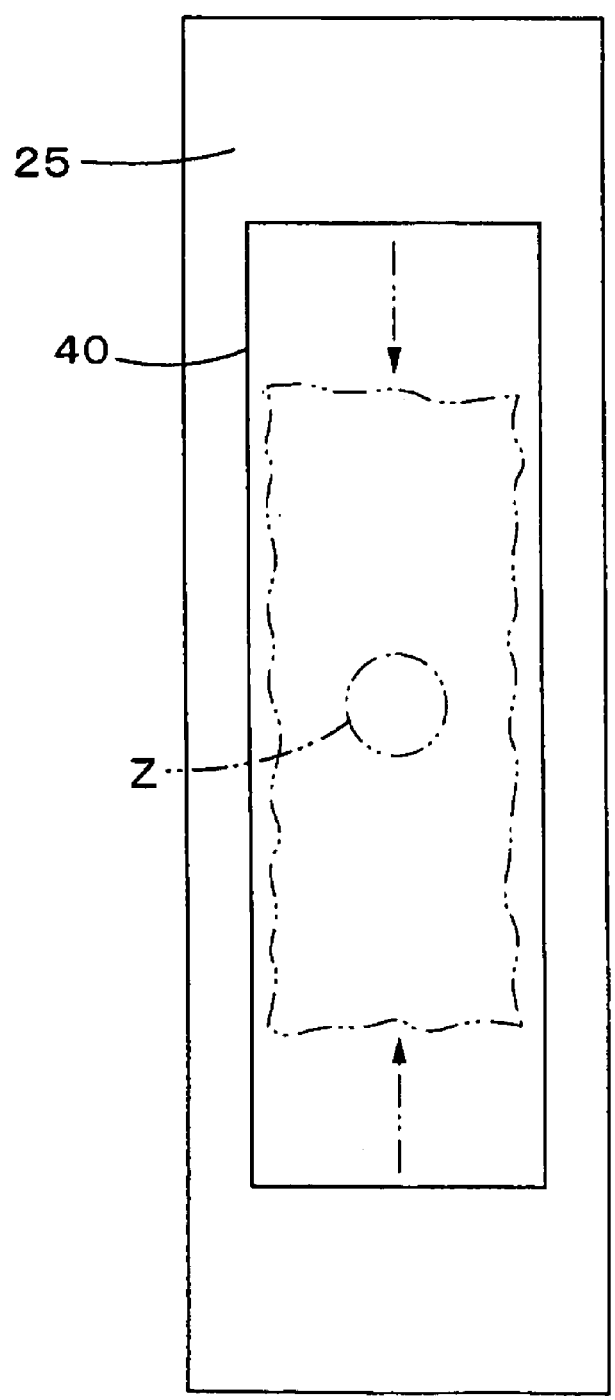
FIG. 22 is a plan view that depicts the important parts (the absorbent member and the control layer) of another embodiment of the absorption control layer.

Alternatively, as shown in FIG. 22, for example, the flat absorption control layer 40 can be formed using a liquid impermeable sheet that shrinks by 50% or more in area when being wet. In this case, the entire absorption control layer 40 constitutes the liquid impermeable range, which is reduced by shrinkage without being dissolved. In FIG. 22, a state of the layer 40 after reduction is indicated by a two-dot chain line. Specific examples of this liquid impermeable sheet are the same as those described in relation to the cylindrical absorption control layer.

Figure 23:
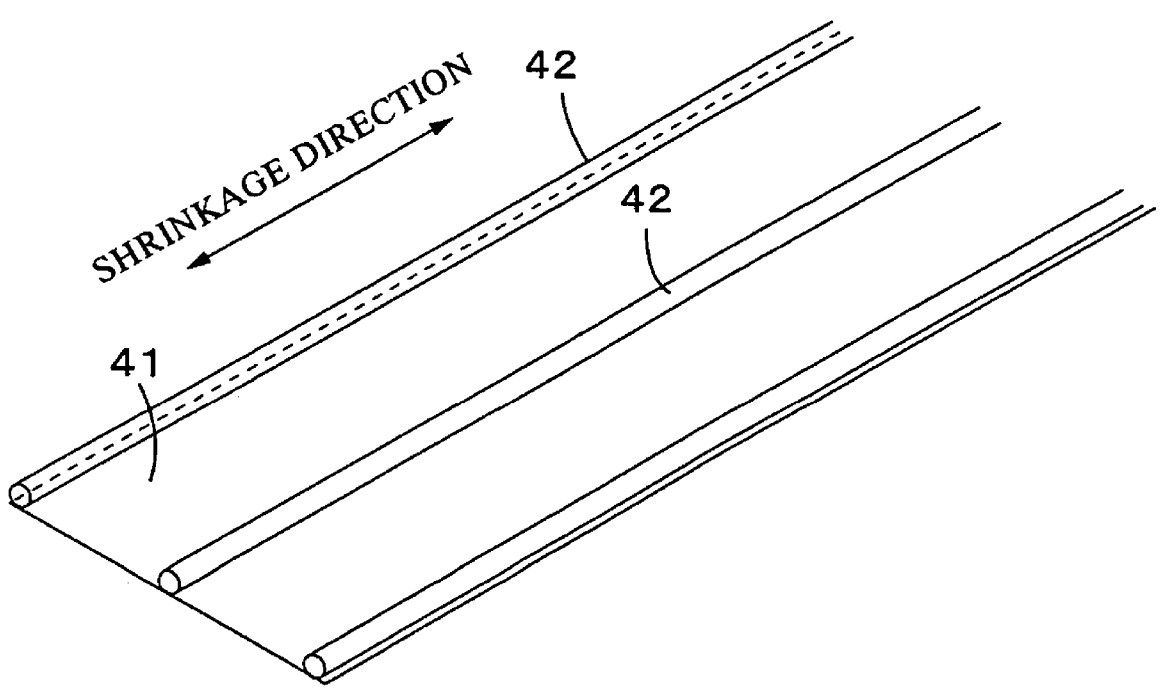
FIG. 23 is a perspective view that depicts another embodiment of the absorption control layer.

Alternatively, as shown in FIG. 23, for example, the flat absorption control layer 40 can be formed by integrating the liquid impermeable sheet 41 with the shrinkable material 42 shrinking when contacting with the body fluid. This absorption control layer 40 may be provided while not being fixed to the article. In consideration of the shrinkage direction of the shrinkable material 42, however, it is preferable that a portion of the layer 40 corresponding to a shrinkage destination position is fixed to the article, e.g., surrounding members such as the body fluid diffusion layer 50 to be described later. By doing so, the liquid impermeable range shrinking in an intended direction can be constituted. In the example of FIG. 23, the shrinkage direction of the shrinkable material 42 is made unidirectional, so that the reduction direction of the liquid impermeable sheet 41 is made unidirectional. Specific examples of the liquid impermeable sheet 41 and the shrinkable material 42 and a method for integrating the sheet 41 with the shrinkable material 42 are the same as those described in relation to the cylindrical absorption control layer. The shrinkable material 42 may be exposed to either the absorbent-side surface or the surface layer 2-side surface of the liquid impermeable sheet 41. It is preferable that the shrinkable material 42 is exposed only to the absorbent-side surface thereof. The liquid impermeable sheet 41 thus configured shrinks following shrinkage of the shrinkable material 42 when the excreted body fluid contacts with the shrinkable material 42.

Figure 24:
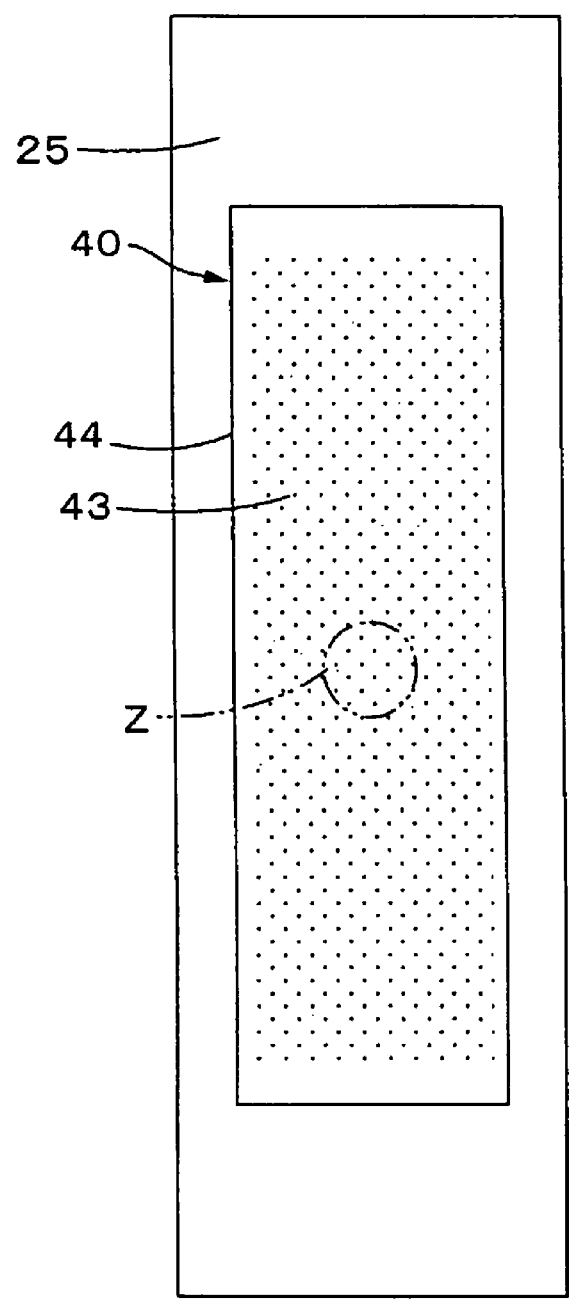
FIG. 24 is a plan view that depicts important parts (an absorbent member and a control layer) of another embodiment of the absorption control layer.
Figure 25:
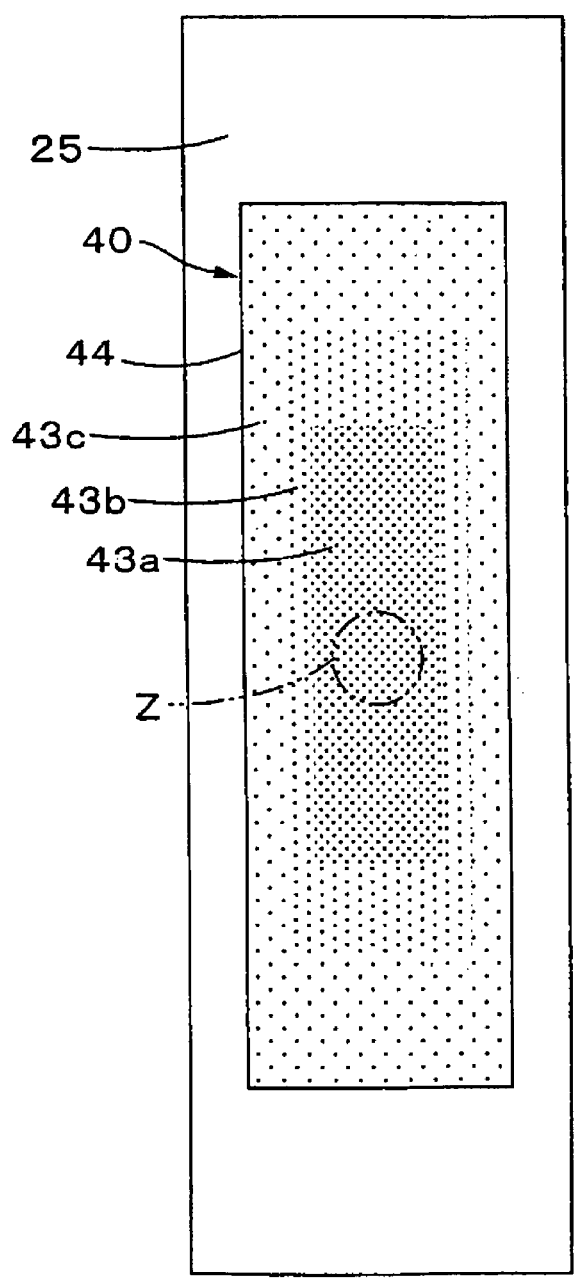
FIG. 25 is a plan view that depicts the important parts (the absorbent member and the control layer) of another embodiment of the absorption control layer.

Alternatively, as shown in FIG. 24, the flat absorption control layer 40 can be formed using the body fluid permeable sheet 44 which is subjected to the water repellent treatment 43 and the water repellency of which is lost when contacting with the body fluid for a predetermined time or more. In this case, the entire sheet does not constitute the liquid impermeable range but a portion having the water repellency corresponds to the liquid impermeable range. If so, since the more body fluid is supplied to surroundings of the water repellent portion 43 even if the water repellent treatment is uniformly performed on the entire liquid impermeable range, the loss of the water repellency progresses from peripheral edges of the water-repellent portion 43 toward the center thereof. A degree of the water-repellent treatment can be changed according to a treatment position. As shown in FIG. 25, for example, the type and the degree of the water-repellent treatment can be changed as indicated by reference symbols 43a to 43c so that the water repellency is lost easily gradually from the center to the outside. The water repellent treatment is the same as that for the cylindrical absorption control layer.

Figure 26:
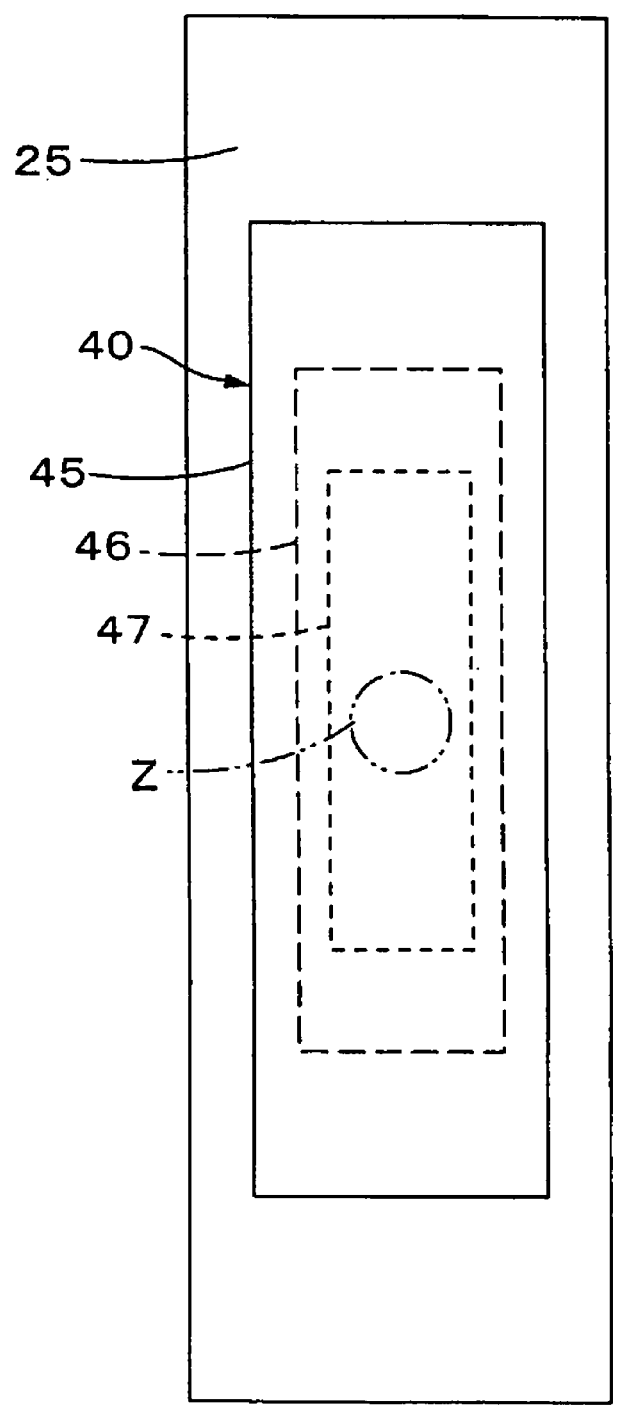
FIG. 26 is a plan view that depicts the important parts (the absorbent member and the control layer) of another embodiment of the absorption control layer.

If the water soluble layer is used as the flat absorption control layer 40, the layer 40 is partially formed to have a multilayer structure using a plurality of water soluble layers 45 to 47 having a common solubility or different solubilities as shown in FIG. 26. It is thereby possible to change a dissolution degree (a dissolution speed and a dissolution range) according to position. In the example shown in FIG. 26, the absorption control layer 40 having a three-layer structure is provided and configured so as to have a smaller area from the surface layer 2-side upper layer 45 toward the leak-proof layer 3-side lower layer 47. In this case, in an initial stage, since only the upper layer 45 is dissolved, the reduction of the liquid impermeable range is moved relatively speedily in a wide range. In an intermediate stage, both the upper and intermediate layers 45 and 46 are dissolved and the liquid impermeable range is then reduced, so that the speed and the range are reduced by one level. In a later stage, all of the upper, intermediate, and lower layers 45 to 47 are dissolved and the liquid impermeable range is then reduced, so that the speed and the range are further reduced.

Figure 27:
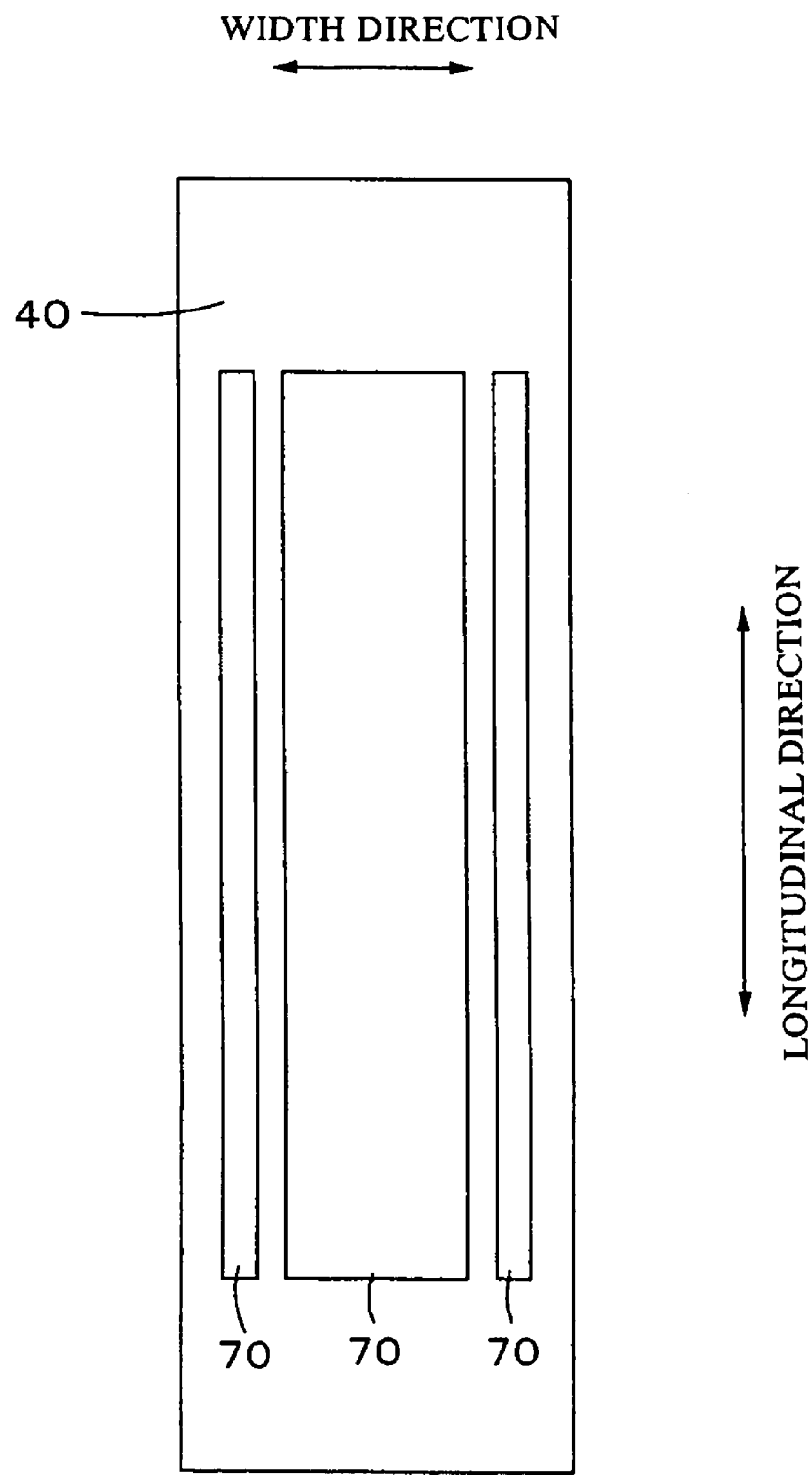
FIG. 27 is a plan view that depicts the important parts (the absorbent member and the control layer) of another embodiment of the absorption control layer.

In addition, one liquid impermeable range of the flat absorption control layer 40 may be provided per article similarly to the cylindrical absorption control layer 40. Alternatively, a plurality of liquid impermeable ranges can be provided at a plurality of locations, respectively. In this case, a plurality of absorption control layers 40 can be provided at a plurality of locations, respectively or a plurality of liquid impermeable ranges can be provided per absorption control layer 40. FIG. 27 depicts this example, in which a plurality of elongated liquid impermeable ranges 70 extending in the longitudinal direction of the article are arranged in the width direction of the article.

If diffusibility of the body fluid is controlled according to the liquid impermeable range, a plurality of liquid impermeable ranges are provided in the flat absorption control layer 40 similarly to the cylindrical absorption control layer 40. By doing so, the liquid impermeability can be set different at each position according to a density of an arrangement of the ranges. For example, an arrangement in which distances between the liquid impermeable ranges are narrower as closer to the center of the article to make it more difficult for the body fluid to reach the absorbent can be adopted.

Figure 28:
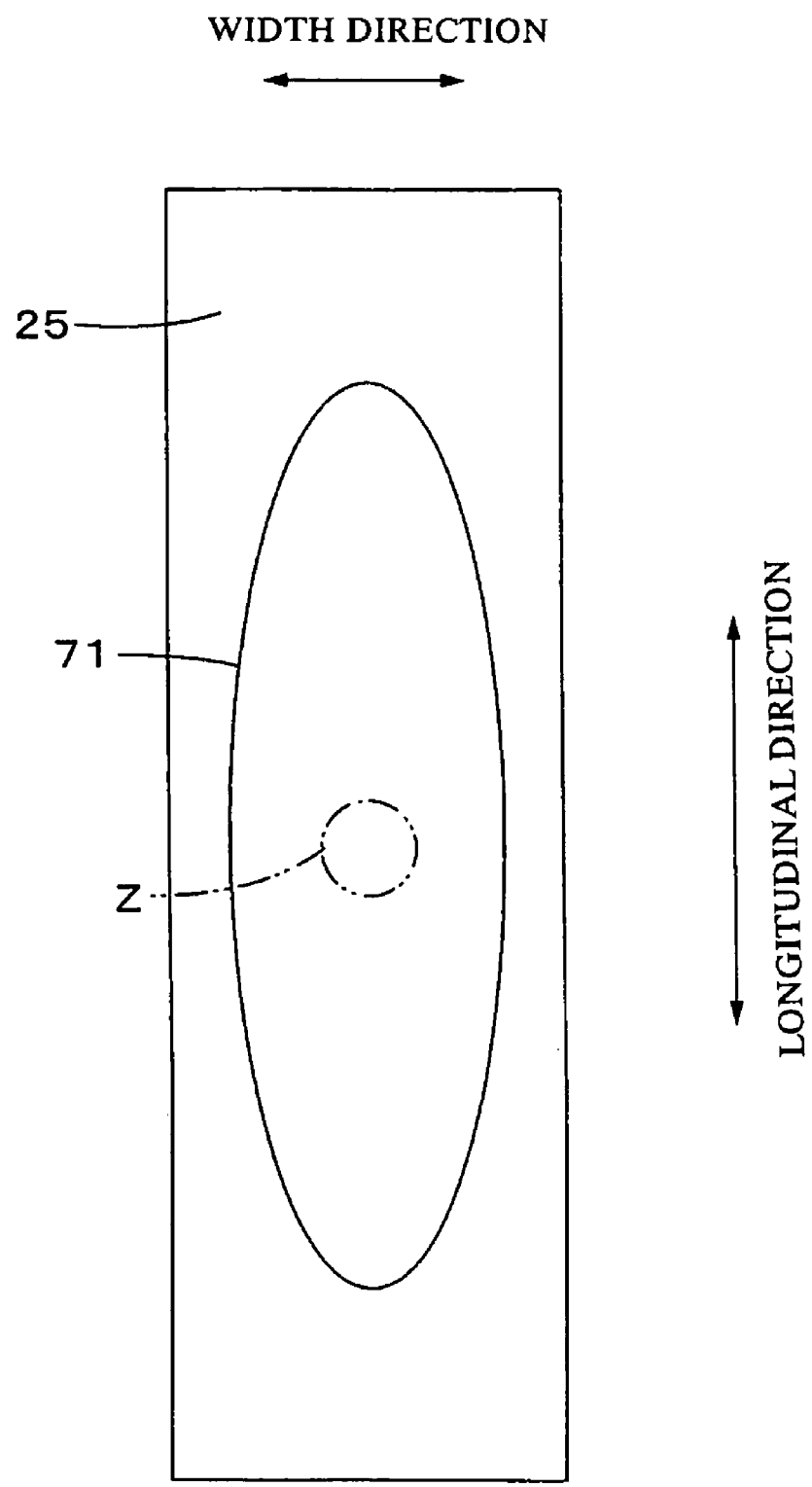
FIG. 28 is a plan view that depicts the important parts (the absorbent member and the control layer) of another embodiment of the absorption control layer.

Further, the form of the liquid impermeable range is not limited to a rectangular form but can be appropriately set. As shown in FIG. 28, for example, in consideration of an ordinary body fluid diffused manner in the body fluid absorbent article, an elliptic liquid impermeable range 71 having a major axis in the longitudinal direction of the article and a center that is the excreted body fluid receiving portion Z can be provided. Alternatively, although not shown, a circular liquid impermeable range having as small diameter as possible to include the excreted body fluid receiving portion so as to eliminate the spot absorption in the receiving portion can be provided.

Figure 29:
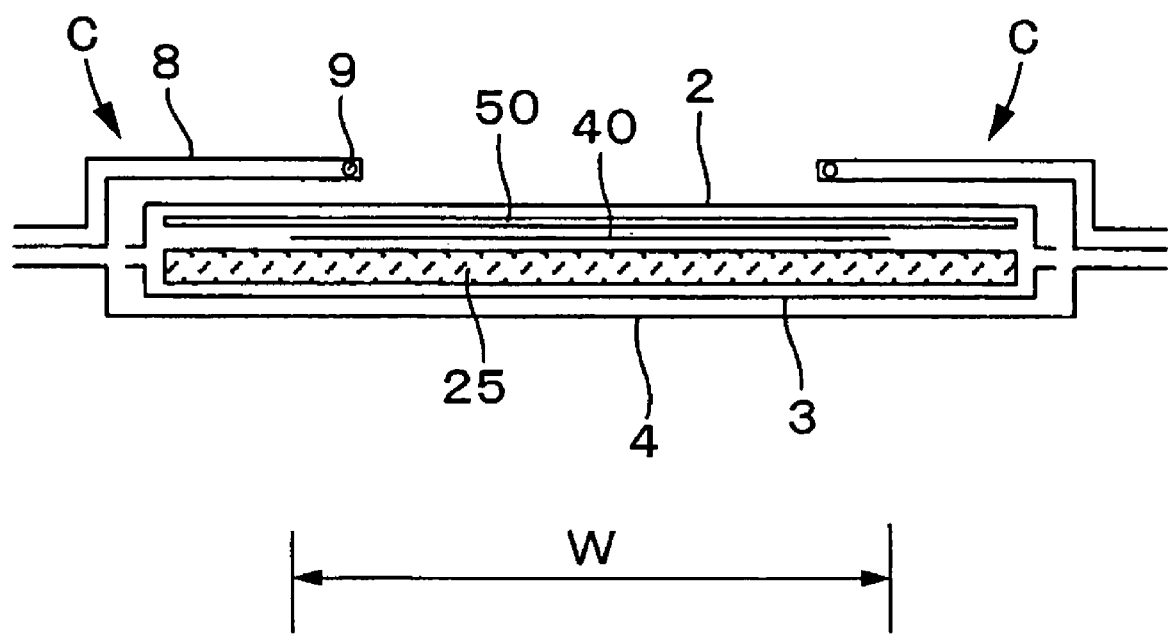
FIG. 29 is a cross-sectional view that depicts another embodiment of the absorption control layer in a width direction.
Figure 30:
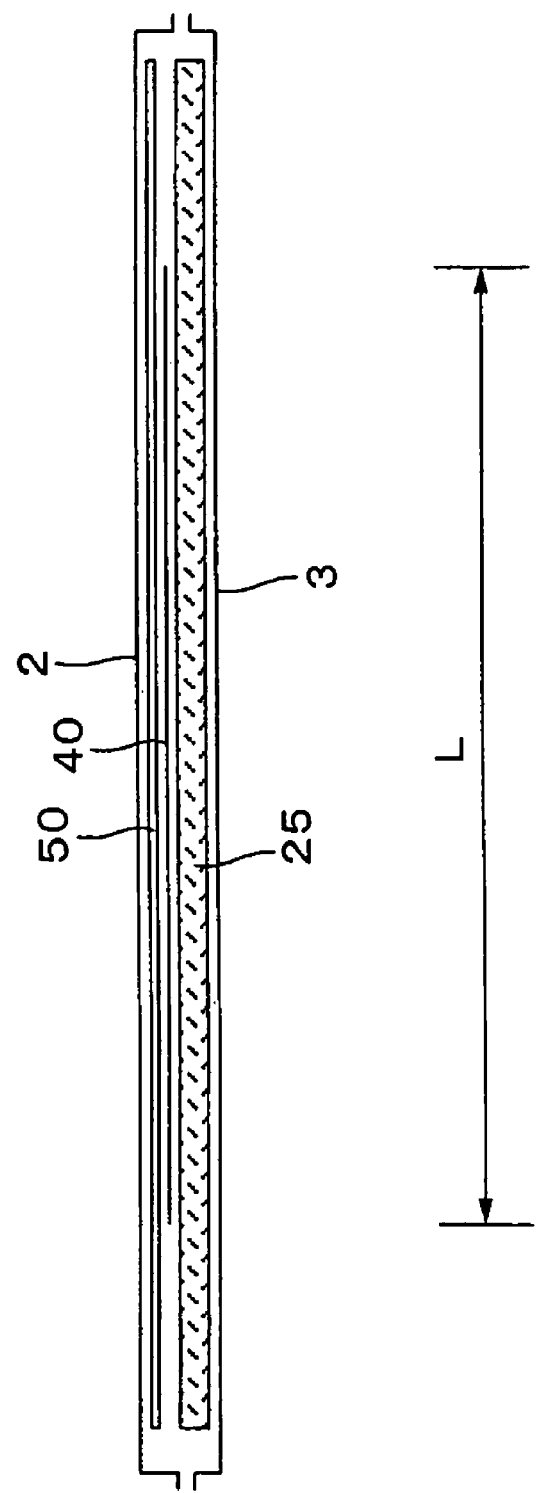
FIG. 30 is a cross-sectional view that depicts another embodiment of the absorption control layer in a longitudinal direction.

As can be understood from these examples, the size and the arrangement of the liquid impermeable range as well as the number of liquid impermeable ranges and the like can be appropriately set according to the intended body fluid diffused state and the reduction degree for every excretion in the flat absorption control layer 40 similarly to the cylindrical absorption control layer 40. In any case, advantages of the present invention can be exhibited. In a body fluid absorbent article shown in FIGS. 29 and 30, for example, the absorbent 25 is provided substantially entirely between the surface layer 2 and the leak-proof layer 3 (that is, in the above-stated body fluid absorbent portion 1) (which configuration is an ordinary configuration). One absorption control layer 40 is provided to correspond to this absorbent 25 between the surface layer 2 and the absorbent 25. In this case, since the area of the absorption control layer 40 is larger, it is preferable to use the flat absorption control layer 40. In addition, the absorption control layer 40 is preferably provided to center around the receiving portion Z, and a length L and a width W orthogonal to the length L preferably fall within ranges of about 50 to 90%, particularly 60 to 80% of those of the absorbent member 25, respectively. By so configuring, it is possible to ensure that the excreted body fluid receiving portion Z is covered by the liquid impermeable range.

If the flat absorption control layer 40 is employed, the boy fluid diffusion layer 50 can be provided similarly to the cylindrical absorption control layer 40. In this case, the body fluid diffusion layer 50 is preferably provided so that the layer 50 can cover the liquid impermeable range and so that peripheral edges of the layer 50 protrude outside of those of the liquid impermeable range. In an ordinary example in which the article includes the surface layer, the body fluid diffusion layer 50 is preferably provided between the surface layer and the absorption control layer. Since specific examples of the body fluid diffusion layer are the same as those described above, they will not be described herein.

In the body fluid absorbent article thus configured, the body fluid passing through the surface layer 2 during the first excretion is blocked by the liquid impermeable range as shown in FIGS. 20(*a*) and 21, for example. Due to this, an entire amount of the body fluid is not supplied to the absorbent 25 but diffused around the liquid impermeable range as indicated by a two-dot chain line, and the body fluid is supplied to the absorbent 25 from surroundings of the liquid impermeable range. This supply range corresponds to a range indicated by reference symbol D1. Since the liquid impermeable range is reduced whenever an excretion of the body fluid occurs, the range is reduced to a range indicated by reference symbol 40' when the next excretion occurs. The entire body fluid during the second excretion is, therefore, supplied to a range D2 that is inside the previous body fluid supply region D1 and that is outside the reduced liquid impermeable range. In the example shown in FIG. 20, the liquid impermeable range is dissolved and disappears during the further next excretion as shown in FIG. 20(*c*), so that the body fluid is supplied to a remaining range D3 including the excreted body fluid receiving portion Z. According to the present invention, the flat absorption control layer 40 having the reduced liquid impermeable range can be adopted similarly to the cylindrical absorption control layer 40.

Moreover, by providing the body fluid diffusion layer 50, the body fluid moving channel is secured by such a flat absorption control layer 40 similarly to the cylindrical absorption control layer. Due to this, the body fluid is instantaneously permeated by the surface layer 2 and the body fluid passing through the surface layer 2 is supplied to the absorbent 25 outside the liquid impermeable range without going backward toward the surface layer 2-side.

In the configuration in which the flat absorption control layer 40 is provided, the body fluid is absorbed by the absorbent 25 from surroundings of the liquid impermeable range. Due to this, by providing a diffusion sheet extending from the region up to an appropriate position between the liquid impermeable range and the absorbent 25, it is possible to adjust extension of the liquid impermeable range up to side surfaces of the absorbent. While this diffusion sheet may be provided separately, it can be configured by, for example, the crape paper wrapping up the outer surface of the fiber assembly that normally constitutes the absorbent 25.

Embodiments of Wall Member

If the absorbent is moved as described in the present invention, it is significant to provide the wall members so as to secure the movement space and the body fluid distribution channel. Appropriate embodiments of the wall member will now be described in detail based on examples of applying the present invention to the body fluid absorbent article including the moving absorbent. Needless to say, the wall member to be described hereinafter is also suitable for the configuration of the absorbent article using the above-stated absorption control layer.

Figure 31:
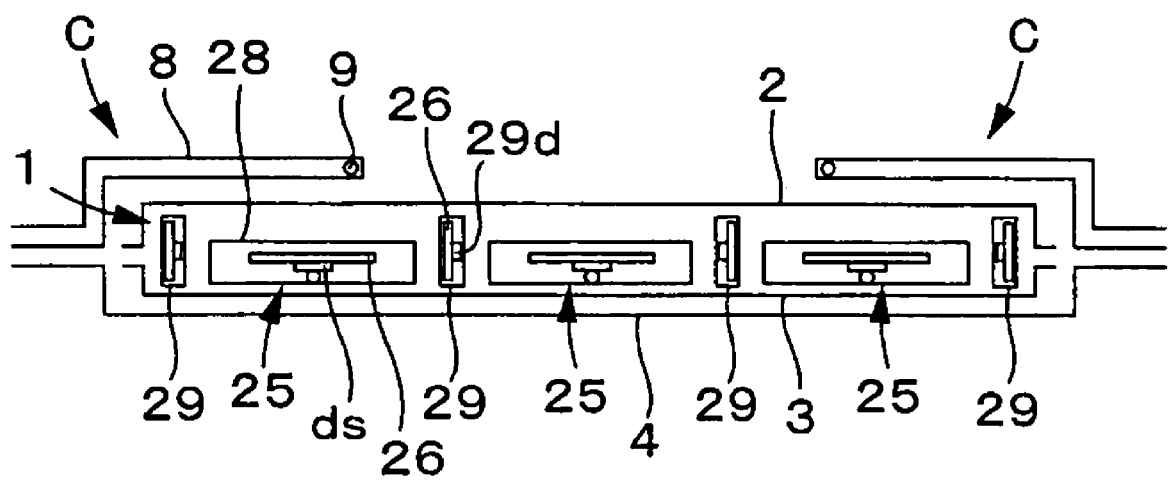
FIG. 31 is a cross-sectional view that depicts important parts of an absorbent article including a wall member in an article width direction.

FIG. 31 is a cross-sectional view that depicts an embodiment of the disposable paper diaper different from the embodiment shown in FIGS. 1 to 5 only in that the absorption control layer 40 is not provided. The body fluid absorbent portion 1 is characterized by being a portion that is provided between the surface layer 2 and the leak-proof layer 3 and that absorbs the body fluid permeated by the surface layer 2. In the body fluid absorbent portion 1, the absorbent 25 that includes a plurality of rows of wall members 29 each consisting of a liquid permeable bag body into which super absorbent polymers are filled at intervals, and that includes the body fluid absorption and holding function and the shrinkage function when contacting with the body fluid is provided.

The wall members 29 are arranged in four rows along the longitudinal direction of the article. A portion between the central wall members 29 corresponds to the body fluid receiving portion Z whereas a portion between the wall members 29 on both sides does not correspond to the body fluid receiving portion Z. The arrangement of the wall members 29 may be appropriately set according to the shrinkage direction of the absorbent 25. Besides the arrangement shown in FIG. 31, the wall members 29 may be arranged in rows parallel to one another along the width direction of the article, or along a radial direction while centering around the body fluid receiving portion Z. It goes without saying that the number of wall members and the number of absorbents can be appropriately increased or decreased.

Figure 32:
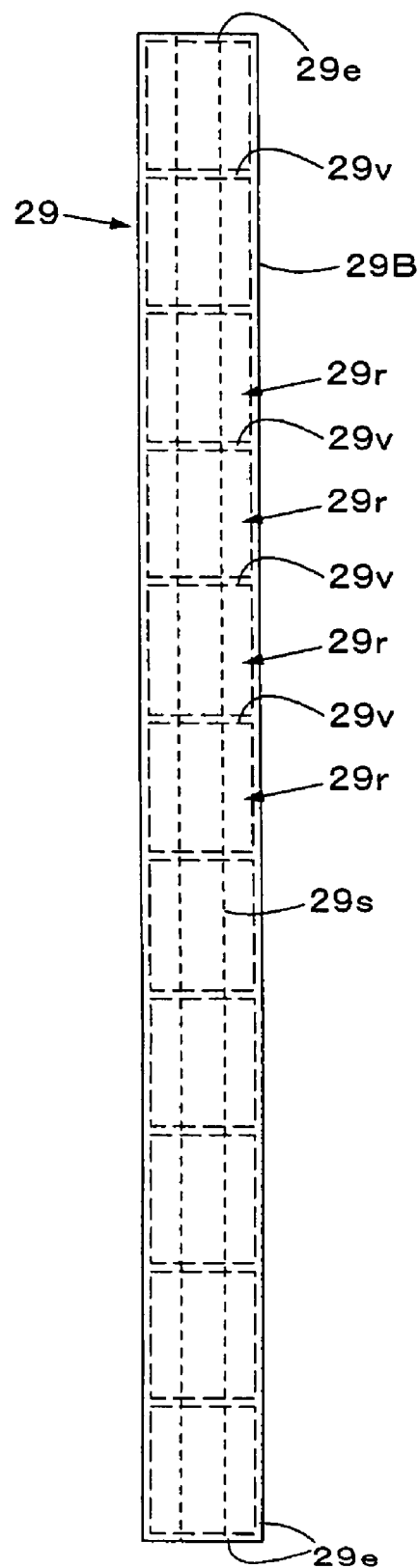
FIG. 32 is a front view of the wall member.
Figure 33:
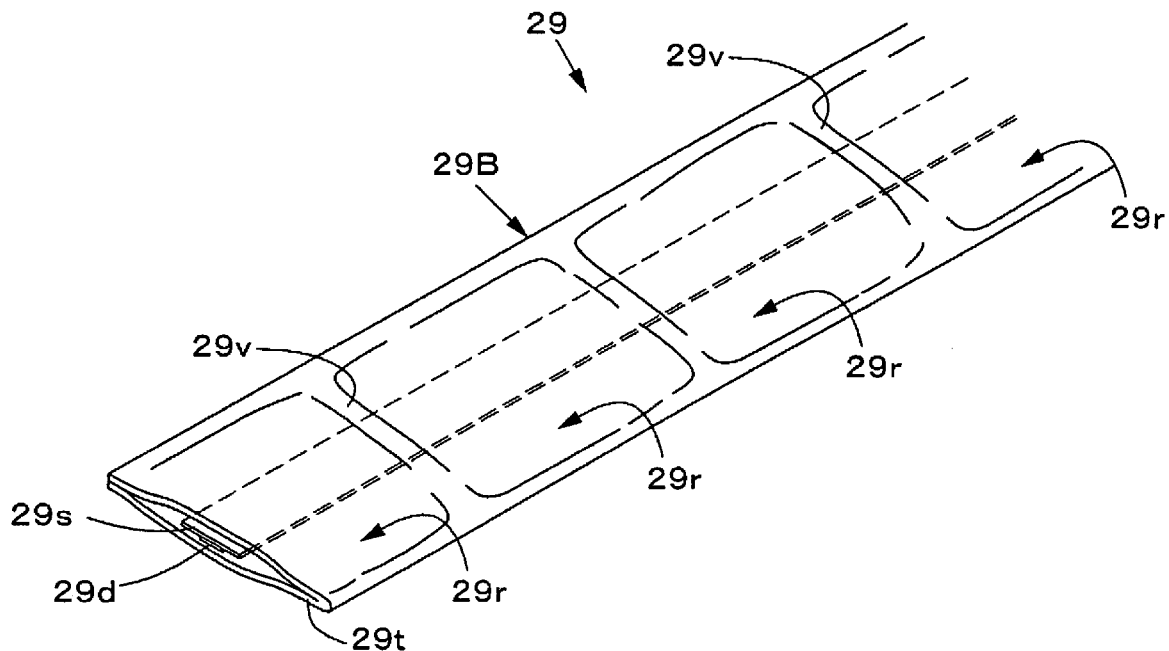
FIG. 33 is a broken perspective view of important parts of the wall member.
Figure 34:
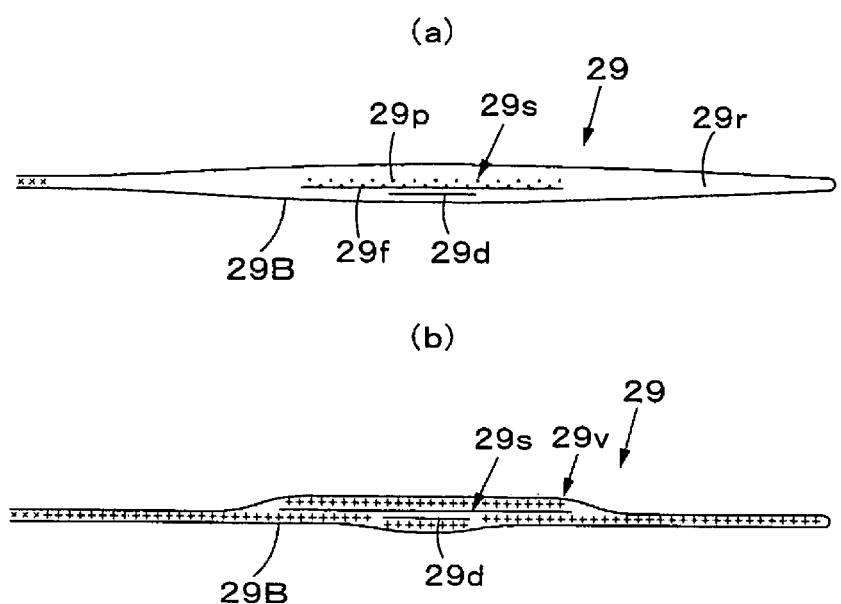
FIG. 34 is a longitudinal sectional view of the wall member.

As shown in, for example, FIGS. 32 to 34, the wall member 29 may mainly consist of a liquid permeable bag body 29B and a super absorbent polymer sheet 29s having super absorbent polymers filled thereinto. Considering that the absorbent 25 is arranged between the wall members 29, the wall members 29 are preferably elongated and thin as shown therein.

A material for the bag body 29B may be arbitrarily selected as long as the material is liquid permeable and satisfies a bursting strength according to the present invention as a bag body. It is particularly preferable to use a liquid permeable hydrophilic nonwoven fabric (a well-known spunbond nonwoven fabric, nonwoven fabric to which a card web is bonded, meltblown nonwoven fabric or composite nonwoven fabric thereof) containing thermoplastic synthetic fibers and having a basis weight of about 15 to 20 $g/m^2$, tissue paper containing synthetic pulp (SWP manufactured by Mitsui Oil Co., LTD or the like) a basis weight of about 15 to 20 $g/m^2$ or the like. From viewpoints of the liquid permeability, a material partially consisting of the liquid permeable nonwoven fabric, a material that is liquid impermeable but that includes permeable pores for permeating the body fluid or the like can be used.

The bag body 29b can be formed either as an integral member without bonded portions or by overlaying one sheet on another sheet and bonding peripheral edges thereof to each other. It is, however, preferable to form the bag body 29b, as shown in FIGS. 32 to 34, by folding one band sheet 29t in a width direction, and overlaying and bonding peripheral edges of folded parts to each other. If so, the bag body 29B can be manufactured more easily. Bonded portions 29e are indicated by symbols × in FIG. 34, and the peripheral edges are bonded to each other by a heat seal, a high frequency seal or an ultrasonic seal so as not to separate them from each other when the bag body 28 contacts with the body fluid.

Further, the bag body 29B shown in the drawings includes many compartments 29r in a longitudinal direction thereof (which compartments r may be omitted, needless to say). Partitions 29v for partitioning these compartments 29r can be formed by, as shown in, for example, FIG. 34(b), bonding two inner surfaces of the bag body 29B to each other in a width direction at intervals in a longitudinal direction of the bag body 29B. The bonded portions of the partitions 29v are indicated by symbols +.

To bond these partitions 29v, a bonding method for separating the bonded portions when the bag body 29B contacts with the body fluid is preferably adopted. Due to this, the partitions 29v are bonded by an adhesive the adhesive power of which is reduced when in contact with the body fluid, e.g., a water dispersible hot melt adhesive mainly consisting of polyvinyl alcohol, polyalkylene oxide or the like, starch, a water soluble adhesive consisting of carboxymethylcellulose or the like. In this case, it is preferable to make a selection of the adhesive, a selection of an adhesive area and a pattern (one of various linear patterns such as spiral, straight, and curved patterns, as well as a surface pattern, a point pattern, and the like), and the like so that the bonding strength during contact with the body fluid is twice or more as high as that during non-contact with the body fluid. In this case, if the partitions 29v contact with the body fluid, the partitions 29v bonded to one another are separated and the super absorbent polymer sheet within each compartment 29r can expand to exceed an initial volume of the compartment 29r, thereby making it more difficult to cause the so-called gel blocking.

Further, the bag body 29B according to the present invention, i.e., the bag body 29B having a bursting strength equal to or higher than 200 $g/cm^2$ according to Mullen Burst Test specified in JIS L 1096A in a standard state can be obtained by selecting a material therefor, and selecting and adjusting a boning method, bonding conditions and the like if the bag body 29B includes the peripheral edge bonded portions 29e. More specifically, a liquid permeable material having a configuration (a thickness, a density, and the like) so that the bursting strength is equal to or higher than the above-stated value is selected. In addition, if a heat seal bonding method or an ultrasonic seal bonding method is adopted, the pattern is changed into an appropriate form such as a net pattern if it is necessary. If a hot melt adhesive bonding method is adopted, then the type of the adhesive is selected and the adhesive area is adjusted. By doing so, the bag body that satisfies these conditions can be obtained. More preferably, the bursting strength of the bag body 29B is equal to or higher than 250 $g/cm^2$.

Figure 35:
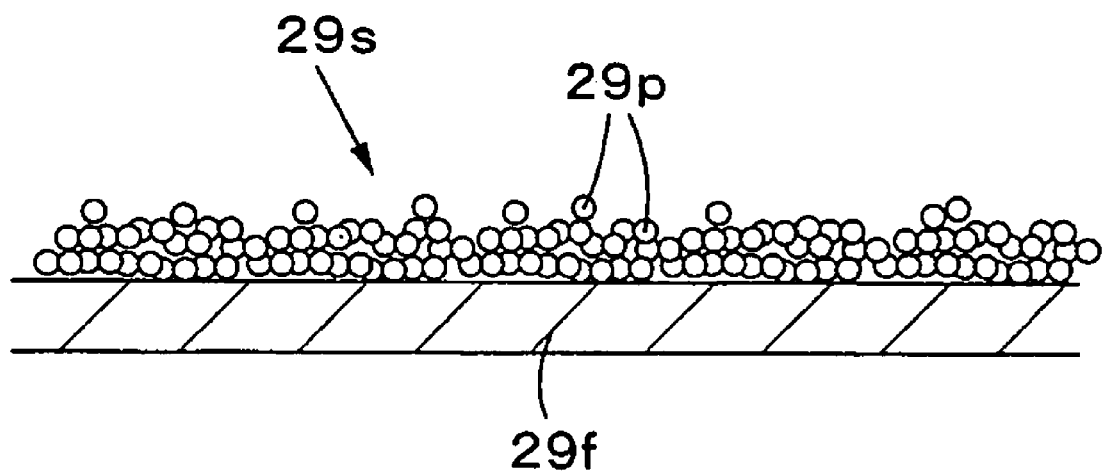
FIG. 35 is a longitudinal sectional view that depicts an embodiment of a super absorbent polymer sheet.
Figure 35:
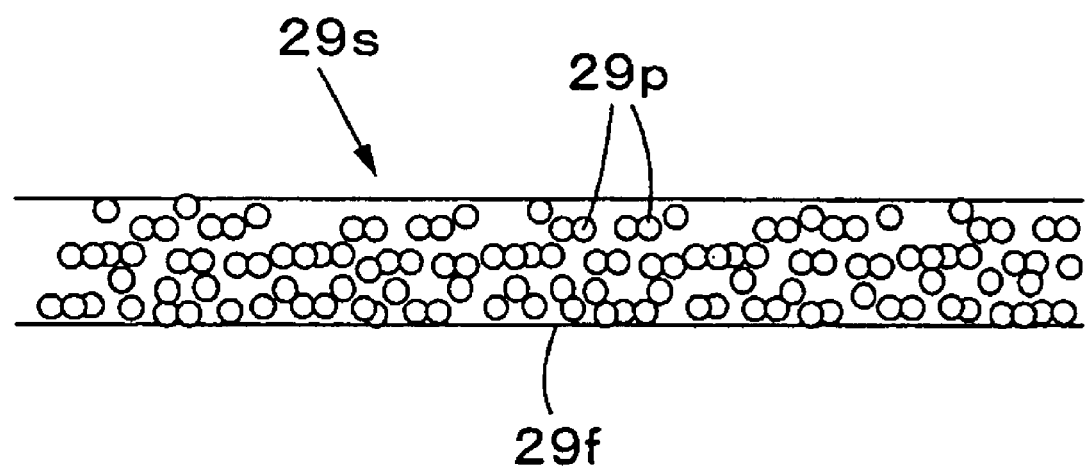

The super absorbent polymer in the form of powder, fiber or the like can be filled into the bag body. In the embodiment shown in the drawings, the super absorbent polymer sheet 29s obtained by fixing super absorbent polymer particles 29p to a sheet carrier 29f such as a nonwoven fabric is filled into the bag body. As this super absorbent polymer sheet 29s, the polymers 29p can be held on an outer surface of the carrier 29f as shown in FIG. 35(a) or, as shown in FIG. 35(b), the carrier 29f consisting of a bulky fiber assembly sheet can be used and the polymers 26p can be held between fibers within the carrier 29f. In the latter case, the polymers 29p can be also held on the outer surface of the carrier 29f. In the former case, the polymers 26p are preferably arranged on at least the surface layer 2-side outer surface of the carrier 26f. Further, a sheet absorbent member configured so that the fiber outer surface of the carrier is coated with a super absorbent polymer layer can be used as the polymer sheet 29s although not shown in the drawings. This sheet absorbent member can be manufactured by impregnating the fiber assembly sheet with a monomer liquid and polymerizing the monomer liquid on the fiber surface by UV radiation or the like.

To make the polymers 29p held on the outer surface of the carrier 29f, the polymers 29p can be bonded onto the outer surface by the hot melt adhesive or the like. Alternatively, moisture can be applied to the polymers 29p, thereby applying an adhesive strength to bond the polymers 29p to the outer surface of the carrier 29f. To make the polymers 26p held between the fibers within the carrier 29f, they can be done so by bonding or adhesion. Alternatively, the polymers 29p may be simply tangled with the fibers mechanically. Further, depending on situations, the polymers 29p may be simply bonded without using any of these holding means. In any case, the super absorbent polymers 29p are held by the carrier 29f at least until the manufacturing of the absorbent is completed, preferably while the product is used until it swells by the body fluid.

An amount of the super absorbent polymers 29p filled into the bag body 29B is preferably set so that a volume of the filled super absorbent polymers 29p after swelling is equal to or greater than a volume of the bag body 29B, particularly the former is 1.1 times or more as great as the latter. Specifically, it is preferable to fill 300 grams or more of the super absorbent polymers 29p per unit area (1 m² of the bag body 29B in a flattened state).

In the wall member 29 shown in the drawings, a body fluid diffusion member 29d is provided within the bag body so as to contact with the super absorbent polymer sheet 29s. The body fluid diffusion member 29d accelerates diffusion of the body fluid in the super absorbent polymer sheet 29s and prevents local absorption of the body fluid. The body fluid diffusion member 29d is preferably provided at a position and near the position in the longitudinal direction of the article to correspond to the body fluid receiving portion Z. If the wall member 29 is elongated as shown in this embodiment, the body fluid diffusion member 29d is preferably provided along the longitudinal direction of the wall member 29 substantially over an entire length of the wall member 29.

A material for the body fluid diffusion member 29d is not limited to a specific one as long as its body fluid diffusibility can relax spot absorption as compared with an instance in which the material is not used. For example, a fiber assembly sheet consisting of synthetic fibers (rayon fibers or the like) surfaces of which are made hydrophilic or consisting of synthetic fibers (rayon fibers or the like) surfaces of which are made hydrophilic and cellulose fibers (pulp fibers or the like), having a basis weight of 30 to 100 g/m², particularly 30 to 50 g/m², a Klemm water absorption of 100 millimeters or more, particularly 150 millimeters or more after ten minutes using a normal saline solution specified in JIS P 8141, and a water holding capacity of 6.0 g/g or more, particularly 7.0 g/g or more can be used. It is particularly suitable to use a fiber assembly obtained by tangling a rayon fiber web by water jet, or a fiber assembly obtained by overlaying pulp fibers on a rayon fiber web and tangling them by water jet.

The "water holding capacity" is the same as that described in the embodiment of the body fluid absorbent article including the absorption control layer. The absorbent is also the same as that described in the embodiment of the body fluid absorbent article including the absorption control layer. They are, therefore, denoted by the same reference symbols and will not be described herein.

Figure 36:
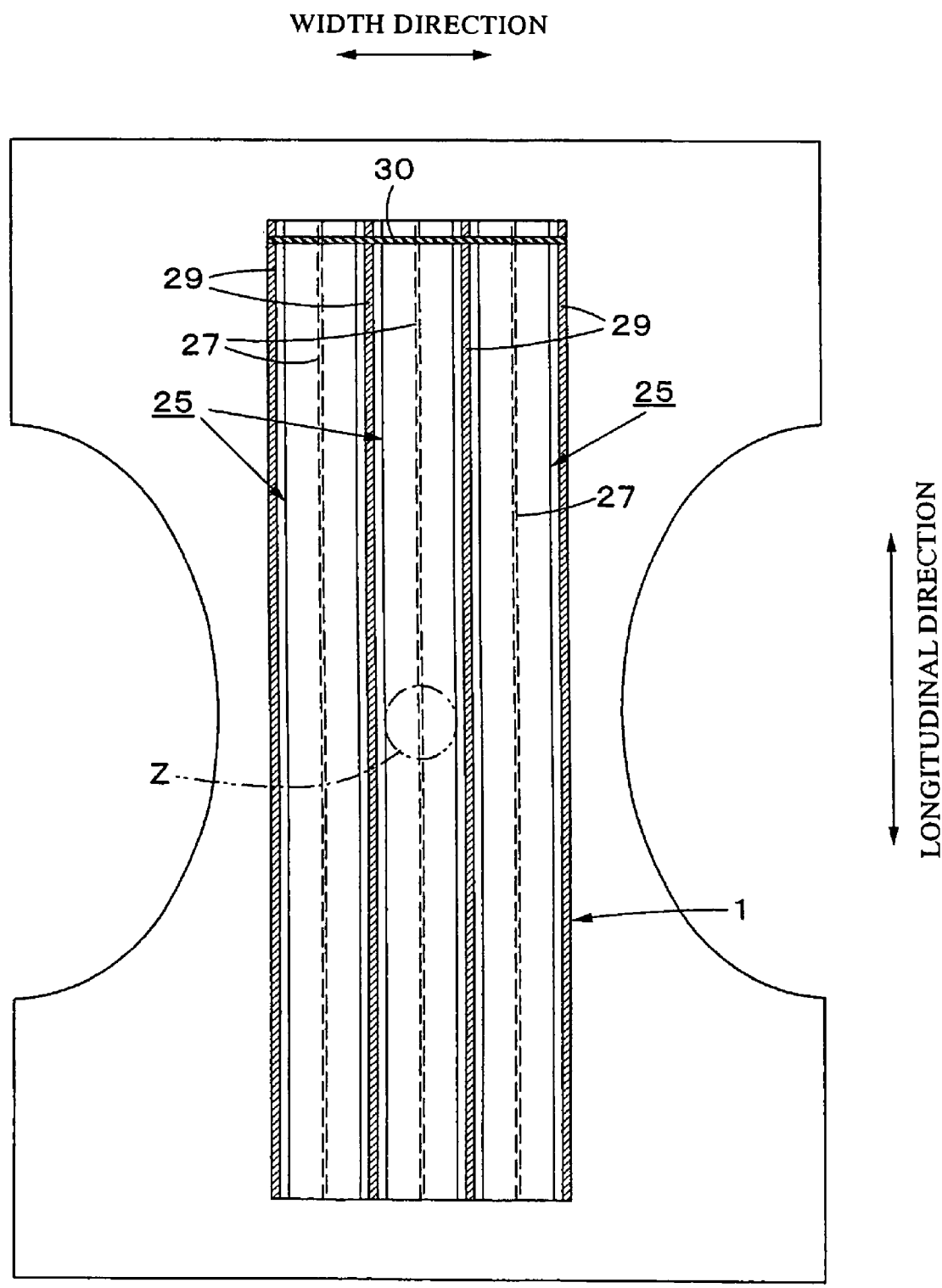
FIG. 36 is a plan view that schematically depicts important parts.
Figure 37:
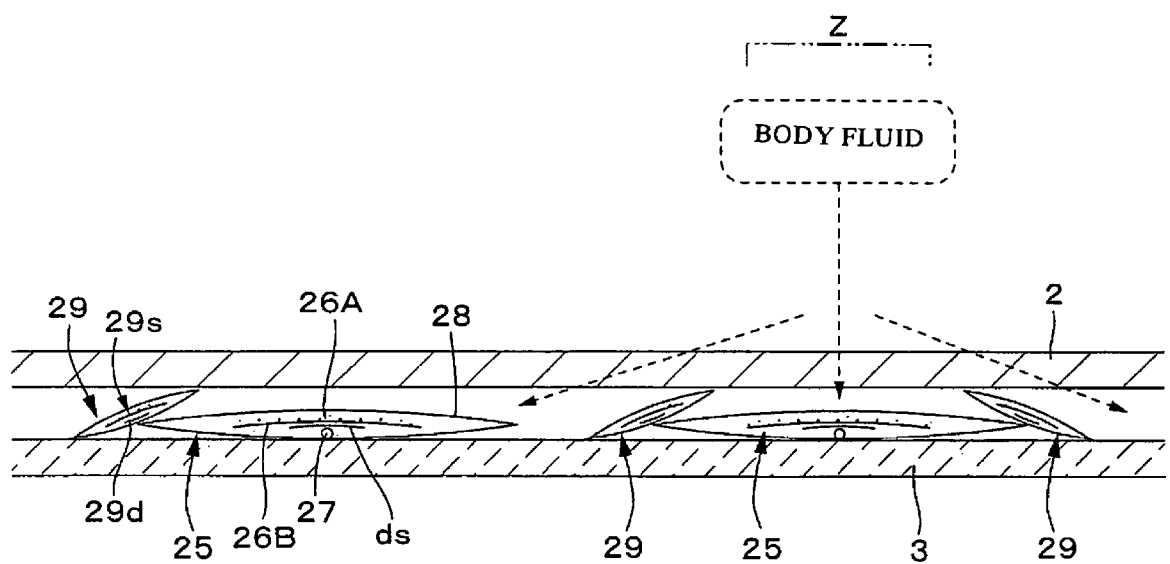
FIG. 37 is a longitudinal sectional view that schematically depicts the important parts.
Figure 38:
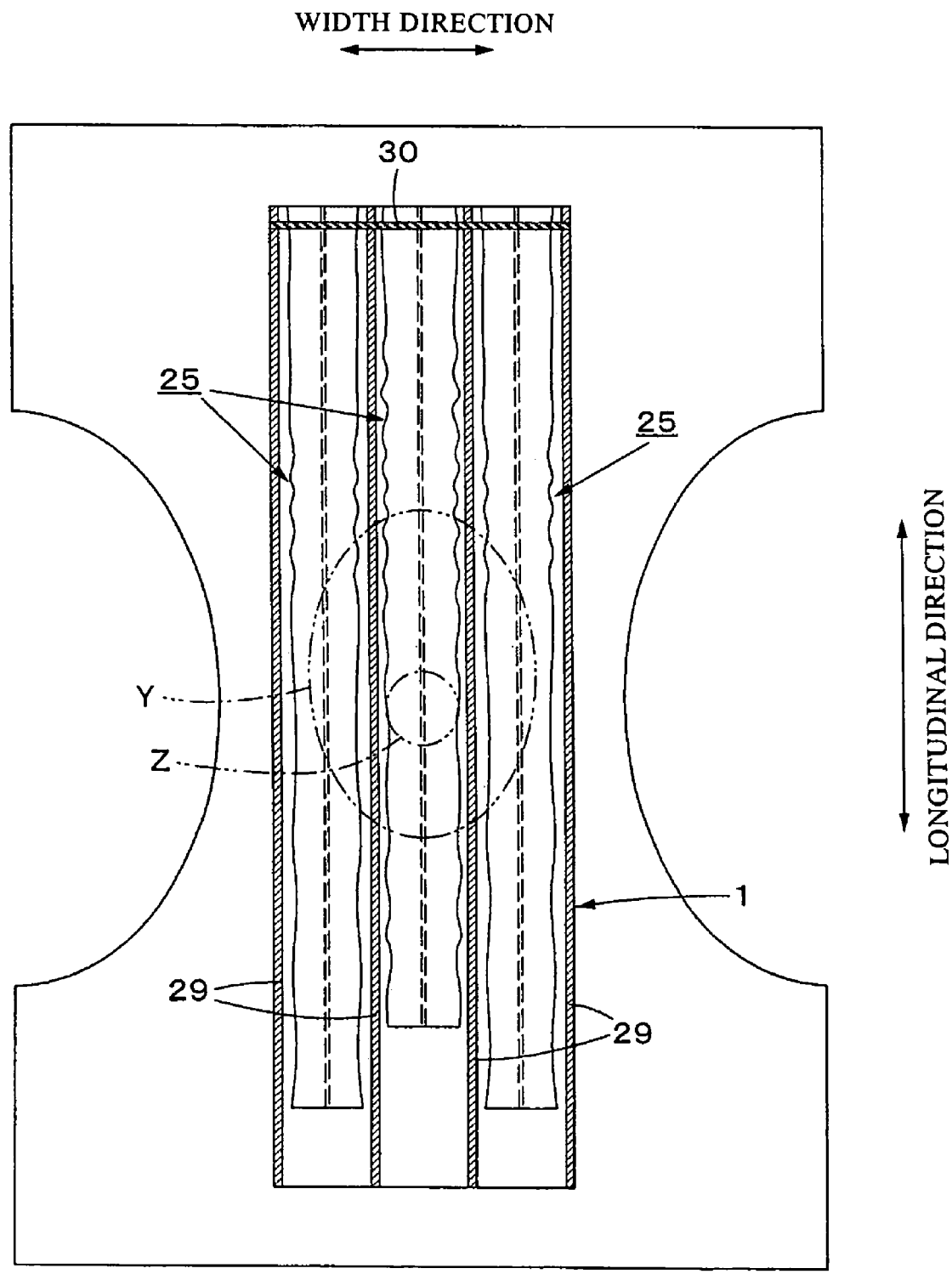
FIG. 38 is a pal view that schematically depicts a moving function.

The paper diaper thus configured exhibits the following functions. As shown in FIGS. 36 and 37, if each absorbent 25 is arranged between the wall members 29, then external pressure is applied to the absorbent 25 by these wall members 29, the shrinking space for the absorbent 25 and the body fluid distribution channel are secured between the surface layer 2 and the leak-proof layer 3. Due to this, even if the wearer sits in a chair while wearing the article, for example, then the shrinking space for the absorbent 25 can be surely secured, the absorbent 25 can be surely and efficiently updated, and the body fluid can be efficiently absorbed. FIG. 38 depicts a state after the absorbent is moved.

Further, the bag body 29B of the wall member 29 according to the present invention has the bursting strength equal to or higher than 200 g/cm² according to Mullen Burst Test specified in JIS L 1096A in a standard state. Due to this, even if the external pressure is considerably high as seen in the adult paper diaper, it is possible to sufficiently resist the pressure. It is, therefore, possible to further ensure smooth shrinkage and movement of the absorbent 25.

Furthermore, if the absorbent 25 is quite long, required to be curvilinearly moved in the hip joint part, and quite high in moving resistance as described in the embodiments, it is necessary to further surely secure the shrinking space. However, even if a large amount of polymers 29p are filled into the bag body 29B and an internal pressure of the bag body 29B is increased, the bag body 29B is sufficiently highly resistible as long as the bag body 29B has the above-stated bursting strength.

The wall member 29 includes the body fluid absorption function by the super absorbent polymers 29p filled into the bag body 29B. Therefore, the wall members 29 enable incidental body fluid absorption, wetting and diffusion in the width direction of the product are inhibited, and wetting and diffusion in the longitudinal direction are accelerated. As a result, it is possible to prevent lateral leakage of the body fluid and make more effective use of the absorbent.

Figure 39:
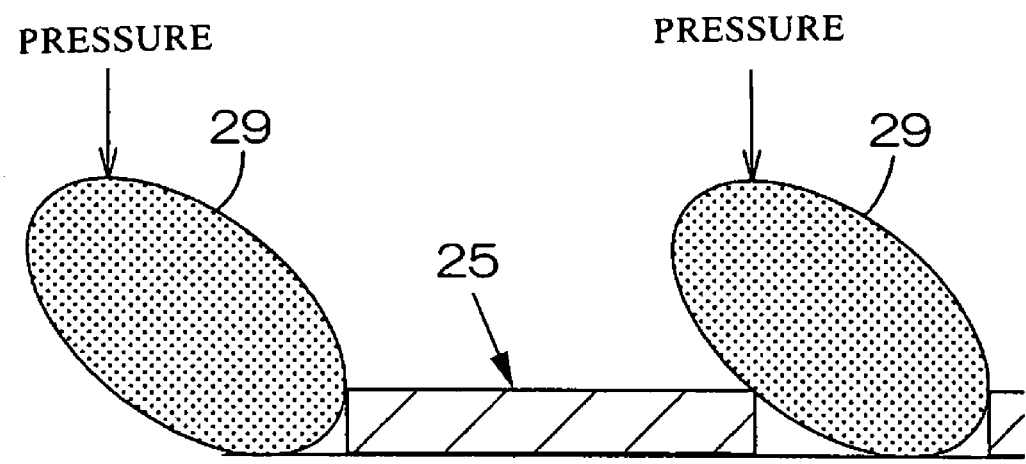
FIG. 39 is an enlarged view of important parts that schematically depicts a function of the wall member.
Figure 40:
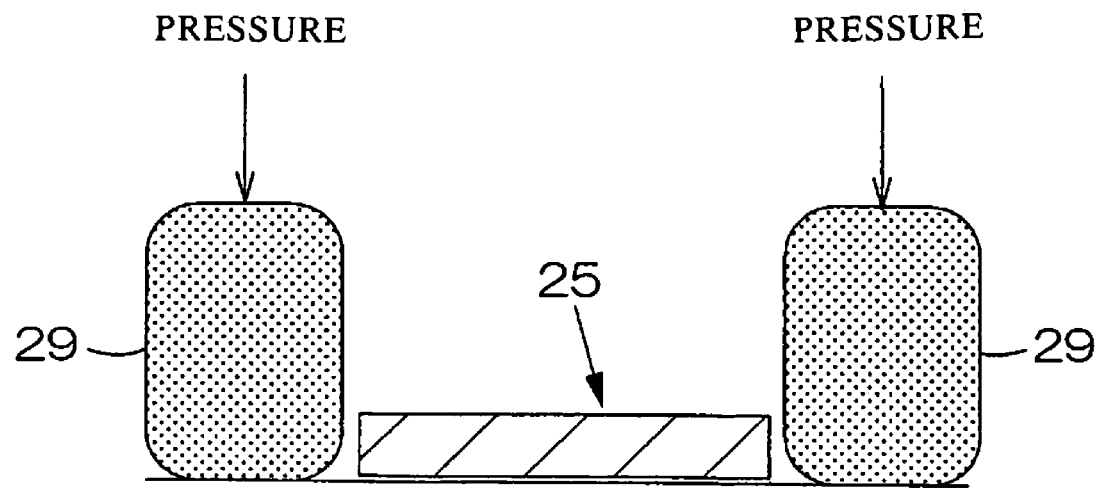
FIG. 40 is an enlarged view of important parts that schematically depicts the function of the wall member.

As evident from comparison of FIG. 39 to FIG. 40, if the bag body 29B of the wall member 29 includes partitions 29v separated when contacting with the body fluid, the compartments 29v are separated when in contact with the body fluid simultaneously with the swelling of the super absorbent polymers 29p after absorbing the body fluid, and a form of a compartment 29r can be spontaneously changed into a stable form. Due to this, it hardly occurs that the wall member 29 falls down sideways or locally protrudes to thereby eliminate the shrinking space for the absorbent 25, and the inherent function of the wall member 29 is not hampered by the absorption of the body fluid but can be always and surely fulfilled.

(Others)

In the currently commercially available paper diaper, an unshrinkable absorbent formed by wrapping up a (semi-rigid) rectangular absorbent core mainly-consisting of flocculent pulp (flap pulp) and having a rigidity to a certain degree in crape paper or the like is provided within the body fluid absorbent portion. The shrinkable member 25 described above can be provided together with this unshrinkable absorbent. If so, the shrinkable member 25 that shrinks can be arranged at an appropriate position either inside or outside the unshrinkable absorbent, more specifically, in a region between a top sheet and the crape paper, between the crape paper and the absorbent core, within the absorbent core, between the crape paper and the leak-proof layer or the like (not shown).

(Others)

The embodiments stated so far can be appropriately changed within the scope of the present invention. For example, the configuration disclosed in a prior application filed by the applicant of the present invention, e.g., that disclosed in the International Publication PCT/JP02/00833 referred to in the Background Art part can be appropriately selected and adopted.

Furthermore, well-known matters and the like can be appropriately adopted within the scope of the present invention. For example, in the currently commercially available paper diaper, the unshrinkable absorbent formed by wrapping up a (semi-rigid) rectangular absorbent core mainly consisting of flocculent pulp (flap pulp) and having a rigidity to a certain degree in crape paper or the like is provided within the body fluid absorbent portion. The shrinkable member 25 described above can be provided together with this unshrinkable absorbent. If so, the shrinkable member 25 that shrinks can be arranged at an appropriate position either inside or outside the unshrinkable absorbent, more specifically, in a region between a top sheet and the crape paper, between the crape paper and the absorbent core, within the absorbent core, between the crape paper and the leak-proof layer or the like (not shown).

The invention claimed is:

1. A body fluid absorbent article, wherein
an absorbent is provided in a body fluid absorbent portion and includes a body fluid absorption and holding function and a shrinkage function when contact with a body fluid;
an absorption control, layer is provided on said absorbent, and a liquid impermeable range of which is reduced whenever a body fluid is excreted;
said absorbent includes a fixed portion fixed to the article, and a free portion that is not fixed to the article,
said absorption control layer is reduced from a fixed portion side of said absorbent toward a free portion side thereof whenever the body fluid is excreted;
said absorbent is elongated and includes said fixed portion on one end thereof, and
said absorption control layer is a cylindrical member including the liquid impermeable range continuous in a circumferential direction and a longitudinal direction, said absorbent being inserted into an inner cavity of said absorption control layer.

2. The body fluid absorbent article according to claim 1, wherein
said liquid impermeable range includes a body fluid receiving portion defined as a range in which the excreted body fluid is received first within said body fluid absorbent portion.

3. The body fluid absorbent article according to claim 1, comprising:
a body fluid diffusion layer which covers said liquid impermeable range and at least a part of which protrudes outside the liquid impermeable range.

4. The body fluid absorbent article according to claim 1, wherein
said absorption control layer is configured so as not to block at least a contact between a fixed portion-side end of the free portion of said absorbent and the body fluid.

5. The body fluid absorbent article according to claim 1, comprising:
a body fluid diffusion layer that extends at least from a body fluid receiving portion defined as a range in which the excreted body fluid is received first within said body fluid absorbent portion to a fixed portion-side end of the free portion of said absorbent.

6. The body fluid absorbent article according to claim 3, comprising:
a body fluid storage portion that is provided in a body fluid receiving portion, said body fluid receiving portion is defined as a range in which the excreted body fluid that contacts the body fluid diffusion layer is received first within said body fluid absorbent portion.

7. The body fluid absorbent article according to claim 1, comprising:
a liquid permeable surface layer provided on a side facing a body skin; and
a leak-proof layer provided on a side away from the body skin, wherein
said body fluid absorbent portion is provided between the surface layer and the leak-proof layer, and
said liquid impermeable range includes at least a body fluid receiving portion defined as the range in which the excreted body fluid is received first within said body fluid absorbent portion.

8. A body fluid absorbent article comprising:
an absorbent provided in a body fluid absorbent portion, said absorbent includes a body fluid absorption and holding function and a shrinkage function when in contact with a body fluid;
an absorption control layer provided on said absorbent, said absorption control layer has a liquid impermeable range that is reduced whenever a body fluid is excreted;
said absorption control layer is a water soluble film having an absorbent-side surface that is not subjected to a water repellent treatment and an opposite surface to the absorbent-side surface that is subjected to the water repellent treatment.

9. The body fluid absorbent article according to claim 8, wherein
said absorption control layer is a liquid impermeable sheet which shrinks by 50% or more in area when wet.

10. The body fluid absorbent article according to claim 8, wherein
said absorption control layer is a liquid impermeable sheet integrated with a shrinkable member that shrinks when in contact with the body fluid.

11. The body fluid absorbent article according to claim 8, wherein
said absorption control layer is a liquid permeable sheet that has been subjected to a water repellent treatment, and the water repellency of the liquid permeable sheet is lost when it contacts body fluid for a predetermined time or more.

12. The body fluid absorbent article according to claim 8, comprising:
a plurality of wall members arranged within said body fluid absorbent portion at predetermined intervals, wherein
said absorbent and said absorption control layer are arranged between the wall members.

* * * * *